US012508160B2

(12) United States Patent
Fellman et al.

(10) Patent No.: US 12,508,160 B2
(45) Date of Patent: Dec. 30, 2025

(54) METHODS FOR TREATING GLAUCOMA

(71) Applicants: RAICO International LLC, Westmont, IL (US); Innovative Glaucoma Consulting LLC, Dallas, TX (US); EyeInnovate LLC, Dallas, TX (US)

(72) Inventors: Ronald L. Fellman, Dallas, TX (US); Davinder S. Grover, Dallas, TX (US); Sebastian S. Grover, Dallas, TX (US); Ravi Nallakrishnan, Willowbrook, IL (US)

(73) Assignees: RAICO International LLC, Westmont, IL (US); Innovative Glaucoma Consulting, LLC, Dallas, TX (US); EyeInnovate LLC, Dallas, TX (US)

( * ) Notice: Subject to any disclaimer, the term of this patent is extended or adjusted under 35 U.S.C. 154(b) by 109 days.

(21) Appl. No.: 18/814,284

(22) Filed: Aug. 23, 2024

(65) Prior Publication Data

US 2025/0064640 A1 Feb. 27, 2025

Related U.S. Application Data

(60) Provisional application No. 63/578,798, filed on Aug. 25, 2023.

(51) Int. Cl.

| | |
|---|---|
| ***A61F 9/007*** | (2006.01) |
| ***A61F 9/008*** | (2006.01) |
| *A61B 90/00* | (2016.01) |

(52) U.S. Cl.

CPC ...... *A61F 9/00781* (2013.01); *A61F 9/00825* (2013.01); *A61B 2090/067* (2016.02);

(Continued)

(58) Field of Classification Search

CPC .............. A61F 9/00781; A61F 9/00825; A61F 2009/00851; A61F 2009/00868;

(Continued)

(56) References Cited

U.S. PATENT DOCUMENTS

| | | | | |
|---|---|---|---|---|
| 9,820,883 B2 * | 11/2017 | Berlin | ................. | A61F 9/00781 |
| 10,123,905 B2 | 11/2018 | Mittelstein | | |

(Continued)

FOREIGN PATENT DOCUMENTS

| | | |
|---|---|---|
| WO | 2021242861 A1 | 12/2021 |
| WO | 2022086754 A1 | 4/2022 |
| WO | 2023219753 A1 | 11/2023 |

*Primary Examiner* — Ahmed M Farah

(74) *Attorney, Agent, or Firm* — Wood, Phillips, Katz, Clark & Mortimer

(57) ABSTRACT

A method of treating glaucoma in an eye includes obtaining a surgical instrument having a cutting means and severing/cleaving an anterior attachment of a portion of trabecular meshwork of the eye proximate to Schwalbe's line with the cutting means while leaving the ciliary muscle tendons attached to the scleral spur of the portion of trabecular meshwork to create a trabecular meshwork leaflet. The surgical instrument including the cutting means is preferably a handheld microsurgical cutting instrument having at least one sharpened edge. Alternatively, the instrument may be an invasive or non-invasive laser cutting instrument with a laser cutting means; a vibratory cutting instrument with a vibratory cutting means; or a thermal cutting instrument with a thermal cutting means. The step of severing the portion of trabecular meshwork is preferably characterized by a linear cleavage plane severing the attachment portion without removing substantially any trabecular meshwork from the eye.

11 Claims, 12 Drawing Sheets

(52) U.S. Cl.
CPC ... *A61B 2217/007* (2013.01); *A61B 2218/002* (2013.01); *A61F 2009/00851* (2013.01); *A61F 2009/00868* (2013.01); *A61F 2009/00891* (2013.01)

(58) Field of Classification Search
CPC ..... A61F 2009/00891; A61B 2090/067; A61B 2217/005; A61B 2217/007; A61B 2218/002; A61B 2218/007
USPC .............................................................. 606/6
See application file for complete search history.

(56) References Cited

U.S. PATENT DOCUMENTS

| | | | | |
|---|---|---|---|---|
| 10,327,947 | B2 | 6/2019 | Kahook | |
| 10,639,195 | B1 | 5/2020 | Mackool | |
| 10,682,254 | B2 | 6/2020 | Kahook | |
| 10,779,991 | B2 | 9/2020 | Kahook | |
| 10,918,521 | B2 * | 2/2021 | Grover | A61B 5/065 |
| 11,266,527 | B2 | 3/2022 | Baerveldt | |
| 2008/0228127 | A1 * | 9/2008 | Burns | A61F 9/00781 604/9 |
| 2010/0262174 | A1 * | 10/2010 | Sretavan | A61F 9/00781 604/20 |
| 2015/0045820 | A1 | 2/2015 | Kahook | |
| 2016/0106589 | A1 | 4/2016 | Mittelstein | |
| 2017/0181892 | A1 | 6/2017 | Kahook | |
| 2018/0133056 | A1 | 5/2018 | Kahook | |
| 2018/0289544 | A1 | 10/2018 | Baerveldt | |
| 2020/0107961 | A1 | 4/2020 | Kahook | |
| 2020/0390600 | A1 * | 12/2020 | Perera | A61F 9/00763 |
| 2021/0000648 | A1 | 1/2021 | Nallakrishnan | |
| 2021/0212859 | A1 | 7/2021 | Koontz | |
| 2021/0322216 | A1 | 10/2021 | Akahoshi | |
| 2022/0087864 | A1 | 3/2022 | Yokoyama | |
| 2023/0000682 | A1 | 1/2023 | Nallakrishnan | |
| 2023/0082713 | A1 * | 3/2023 | Ianchulev | A61F 9/00781 606/107 |
| 2023/0190527 | A1 | 6/2023 | Espaillat | |
| 2023/0363943 | A1 | 11/2023 | Tanito | |
| 2024/0407949 | A1 * | 12/2024 | Fellman | A61F 9/00781 |

* cited by examiner

METHODS FOR TREATING GLAUCOMA

PRIORITY

This application claims priority to U.S. provisional application Ser. No. 63/578,798, filed Aug. 25, 2023, the entire contents of which is incorporated herein by reference.

FIELD OF THE INVENTION

The present invention relates to methods for performing ophthalmological procedures for treatment of eye diseases, such as glaucoma, and more particularly to methods to facilitate an anterior goniotomy procedure.

BACKGROUND OF THE INVENTION

Goniotomy was initially described as a surgical procedure to treat congenital and developmental glaucomas that are caused by a developmental abnormality in the trabecular outflow system. As a result of this abnormality, the trabecular meshwork itself becomes thicker and these changes lead to elevated intraocular pressure that can damage the internal structures of the eye, including the optic nerve leading to the development of glaucoma. Later, goniotomy was found to lower eye pressure in adults.

The purpose of a goniotomy is to selectively cleave the abnormal trabecular tissue in order to improve the flow of aqueous from the eye, which in turn lowers the intraocular pressure (IOP). Lowering the IOP helps to stabilize the enlargement of the cornea and the distension and stretching of the eye that often occur in congenital/developmental glaucoma. Importantly, once the aqueous outflow improves, damage to the optic nerve is halted and may be reversed. The patient's visual acuity may improve after surgery. In adults, goniotomy cleaves open diseased outflow tissues similar to its effect of decreasing outflow resistance in the childhood glaucomas.

The goniotomy procedure can restore normal drainage of aqueous humor from the eye by cleaving a segment of the trabecular meshwork, thus allowing the aqueous humor to drain through the open area from which the strip of trabecular meshwork has been cleaved. The goniotomy procedure and certain prior art instruments useable to perform such procedure are described in U.S. Pat. No. 6,979,328, hereby incorporated by reference in its entirety.

U.S. Pat. Nos. 4,846,172 A and 6,241,721 B1 teach invasive laser ablation instruments and methods for forming artificial passageways in the trabecular meshwork while U.S. Pat. No. 6,059,772 A, U.S. Patent Application Publication No. US 2020/0330266 A1, and International Patent Application Publication No. WO 2020/018243 A1 teach non-invasive laser ablation instruments and methods for forming artificial passageways in the trabecular meshwork, and all of said prior art documents are hereby incorporated by reference in their entireties as if fully set forth herein. Generally, these prior art disclosures taught the boring of artificial holes or passageways into or through the trabecular meshwork to improve flow therethrough with or without the implantation of a shunt or other artificial passageway in the eye.

At present there remains a need in the art for the development of improved, easy to use, inexpensive, minimally invasive instruments and methods to perform the goniotomy type glaucoma treatment procedures, or other similar procedures, to reduce intraocular pressure with long-lasting effects to reduce or eliminate follow-up procedures and/or to reduce the number of intraocular pressure reducing medications prescribed to a patient.

BRIEF SUMMARY OF THE INVENTION

In accordance with one broad form of the present invention, a method of treating glaucoma in an eye is disclosed. The method includes the step of obtaining a surgical instrument including a cutting means and the step of severing (i) an anterior attachment of a portion of the trabecular meshwork of the eye proximate to Schwalbe's line and (ii) the inner wall of Schlemm's Canal with the cutting means of the surgical instrument while leaving the ciliary muscle tendons attached to the scleral spur and the elastic network of the portion of the trabecular meshwork to create a trabecular meshwork/inner wall of Schlemm's Canal leaflet.

In one form of the present invention, the step of severing the anterior attachment of a portion of trabecular meshwork and the inner wall of Schlemm's Canal is characterized by a linear cleavage plane severing the attachment portion and the inner wall of Schlemm's Canal without removing substantially any of the trabecular meshwork from the eye.

According to another form of the present invention, the step of severing the anterior attachment of a portion of trabecular meshwork and the inner wall of Schlemm's Canal is characterized by a linear cleavage plane severing the attachment portion and the inner wall of Schlemm's Canal, which is laterally spaced from, and sparing/preserving, the intracanalicular valves and other intracanalicular structures of the outflow system of the eye.

In one preferred form of the present invention, the trabecular meshwork/inner wall of Schlemm's Canal leaflet rotates in a posterior direction along the optical axis of the eye upon severing the anterior attachment of a portion of trabecular meshwork.

In one preferred form of the present invention, the step of severing the anterior attachment of a portion of trabecular meshwork and the inner wall of Schlemm's Canal is characterized by forming an opening angle of between about 4 degrees and about 45 degrees defined between the trabecular meshwork/inner wall of Schlemm's Canal leaflet and the outer wall of the Schlemm's Canal.

In another form of the present invention, the surgical instrument including a cutting means is selected from one of: a handheld microsurgical cutting instrument having at least one sharpened edge; an invasive or non-invasive laser cutting instrument; a vibratory cutting instrument; or a thermal cutting instrument.

According to still another form of the present invention, the method includes the further step of applying an irrigating fluid to the trabecular meshwork/inner wall of Schlemm's Canal leaflet.

In another form of the present the invention, the method includes the step of imaging an angle between the leaflet and the inner wall of Schlemm's Canal. In one form, the method includes the step of measuring a first angle at a temporal location of an unoperated portion of the eye, wherein the first angle is defined between an intersection of a first line extending parallel to the inner sclera posterior to the scleral spur and a second line extending parallel to the scleral spur (as viewed in an OCT image extending in a vertical plane containing the optical axis). The method further includes the step of measuring a second angle at a nasal location of an operated portion of the eye, wherein the second angle is defined between an intersection of a first line extending parallel to the inner sclera posterior the scleral spur and a second line extending parallel to the scleral spur. The method includes the further step of comparing the first and second angles.

In one form of the present invention, the step of severing the anterior attachment of a portion of trabecular meshwork and the inner wall of Schlemm's Canal further comprises severing the anterior attachment of a portion of trabecular meshwork and the inner wall of Schlemm's Canal between about 90 degrees and about 180 degrees around the periphery of the eye. More preferably, the trabecular meshwork and the inner wall of Schlemm's Canal is severed about 120 degrees around the periphery of the eye relative to the optical axis of the eye.

In accordance with another broad form of the present invention, a method of treating glaucoma in an eye is disclosed. The method comprising the steps of: obtaining a surgical instrument including a cutting means; severing (i) an anterior attachment of a portion of the trabecular meshwork of the eye proximate to Schwalbe's line and (ii) the inner wall of Schlemm's Canal with the cutting means of the surgical instrument in a linear cleavage plane while leaving the ciliary muscle tendons attached to the scleral spur and the portion of the trabecular meshwork to create a trabecular meshwork/inner wall of Schlemm's Canal leaflet; and then leaving substantially all trabecular meshwork within the eye.

BRIEF DESCRIPTION OF THE DRAWINGS

In the accompanying drawings forming part of the specification, in which like numerals are employed to designate like parts throughout the same.

FIG. 13A shows the formation of a trabecular meshwork leaflet or flap at 1-month post operation;

FIG. 13B shows the formation of a trabecular meshwork leaflet or flap at 12-months post operation;

FIG. 13C shows the formation of a trabecular meshwork leaflet or flap at 17-months post operation;

FIG. 13D shows the classic formation of a trabecular meshwork leaflet or flap;

FIG. 13E shows the leaflet in greater detail;

FIG. 13F shows the leaflet in greater detail;

FIG. 15 shows the SLAM measurement of the temporal angle; FIG. 16 shows the SLAM measurement of the nasal angle.

DETAILED DESCRIPTION OF THE PREFERRED EMBODIMENTS

Figure 1:
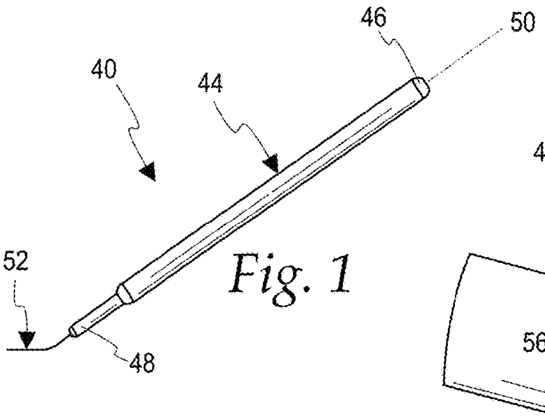
FIG. 1 is a left-side elevation view of a first embodiment of a surgical instrument for performing the method according to the present invention, wherein the instrument has the form of a handheld cutting instrument with a sharpened cutting edge.

With reference to FIGS. 1-6, in accordance with a first illustrated embodiment of a surgical instrument for performing the method of the present invention, which is configured as a hand-held, manually operated cutting instrument 40 which includes a hand piece or hand grip 44 for being gripped by a user of the instrument 40. The grip 44 has an elongated configuration, including a proximal end 46 and a distal end 48 defining a hand grip axis 50 extending therebetween. FIGS. 1-6 show a first variation of the instrument 40 for use as a right-angled instrument. FIGS. 7-12 show a left-angled variation of the instrument 40A, which will be discussed in greater detail below. It is further contemplated that this embodiment of the instrument 40 may also be configured as a non-angled, straight instrument. Each of these variations of the instrument 40 and 40A are configured to contact specific angles, arcs, or portions of the trabecular meshwork of a patient's eyes, as will be discussed in detail below. The hand grip 44 can be provided with either a rounded or a flattened configuration and is preferably knurled for ease of grip. Furthermore, the hand grip 44 may be a cannula hub or fitting with means for being attached to a larger machine, irrigation system, or commercial irrigating handpiece (e.g., screw threading, snap-fit connection, luer lock connection, friction fit, locked, etc.). The numbered features of the embodiments of the instruments 40 and 40A illustrated and discussed herein are designated generally with a number where such features are analogous in structure and function.

Figure 4:
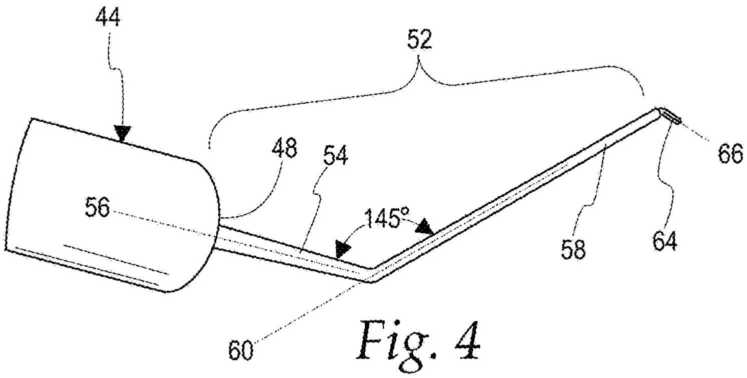
FIG. 4 is an enlarged, isometric view, of the operative, distal tip portion of the instrument of FIG. 3.
Figure 2:
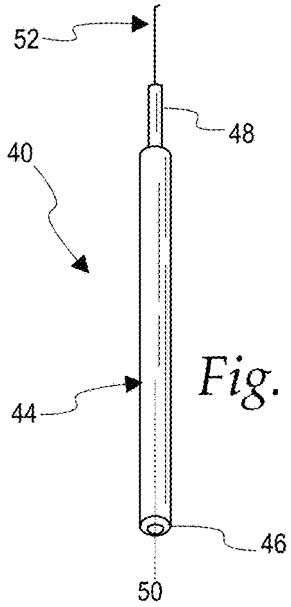
FIG. 2 is a top plan view of the instrument of FIG. 1.

With reference now to FIG. 4, the instrument 40 includes a tip 52 that extends, either directly from the distal end 48 of the hand grip 44, or indirectly from the distal end 48 of the hand grip 44 via one or more straight or angled shank portions depending on the right, left, or straight designed use of the instrument 40.

In the illustrated first preferred embodiment of the instrument 40 for performing the steps of the method of the present invention, the tip 52 includes a base portion 54 that extends from the distal end 48 of the hand grip 44 and defines a base portion axis 56 through its geometric center. The base portion axis 56 is substantially parallel to, and coincident with, the central axis 50 of the hand grip 44. The tip 52 further includes an intermediate portion 58 extending from the base portion 54 along an intermediate portion axis 60 that is transverse or angled relative to the base portion axis 56. Preferably, the intermediate portion axis 60 is angled between about 130 degrees and 160 degrees relative to the base portion axis 56, and more preferably angled about 145 degrees. The tip 52 includes a terminal portion 64 extending from the intermediate portion 58 along a terminal portion axis 66 that is transverse to the intermediate portion axis 60. Preferably, the terminal portion axis 66 is angled between about 90 degrees and about 140 degrees relative to the intermediate portion axis 60, and more preferably is angled about 120 degrees. The terminal portion 64 includes cutting means for creating a trabecular leaflet at, or just minimally posterior to or below, Schwalbe's line in an eye. The inventors have found that increasing the angle between axes 66 and 60 from about 90 degrees to about 120 degrees greatly improves the user's ability to perform the surgical operation of creating the leaflet.

With reference to FIGS. 13A-13F, a series of optical coherence tomography images of an eye 100 that has been operated upon in accordance with the method of the present invention with the surgical instrument 40. Directions referenced herein are generally taken relative to the optical axis 110 (or a line parallel thereto) of such an eye 100, wherein the anterior direction is axially upwardly in FIGS. 13A-13F away from the optic or lens of the eye, and the posterior direction is axially downwardly in FIGS. 13A-13F toward the optic of the eye. FIGS. 13A-13F show the cornea 120, iris 130, and the opening of Schlemm's Canal 140 of the eye 100. The inventors have found that the instrument 40 disclosed herein is advantageously configured to safely and efficiently incise the trabecular meshwork tissue directly below Schwalbe's line and the inner wall of Schlemm's Canal to allow the separated trabecular meshwork or leaflet 150 to drop away from the cornea 120 in the posterior direction toward the iris 130. More specifically, the method severs the anterior attachment portion of the trabecular meshwork leaflet 150 proximate Schwalbe's line while leaving the ciliary muscle tendons attached to the scleral spur of the trabecular meshwork to form the leaflet 150. The incision may be characterized by a substantially linear cleavage plane that severs the attachment portion of the trabecular meshwork leaflet 150, but which does not remove substantially any (i.e., any appreciable visible tissue) meshwork from the patient's eye. Furthermore, the cleavage plane is laterally spaced from the intracanalicular valves of the outflow system of the eye, sparing these structures. The trabecular meshwork leaflet or flap 150, which extends an angle or arc around the periphery or circumference of the yet relative to the optical axis 110, may improve flow through the Schlemm's Canal 140 to lower intraocular pressure and reduce the medications required by a patient with glaucoma.

Figure 13A:
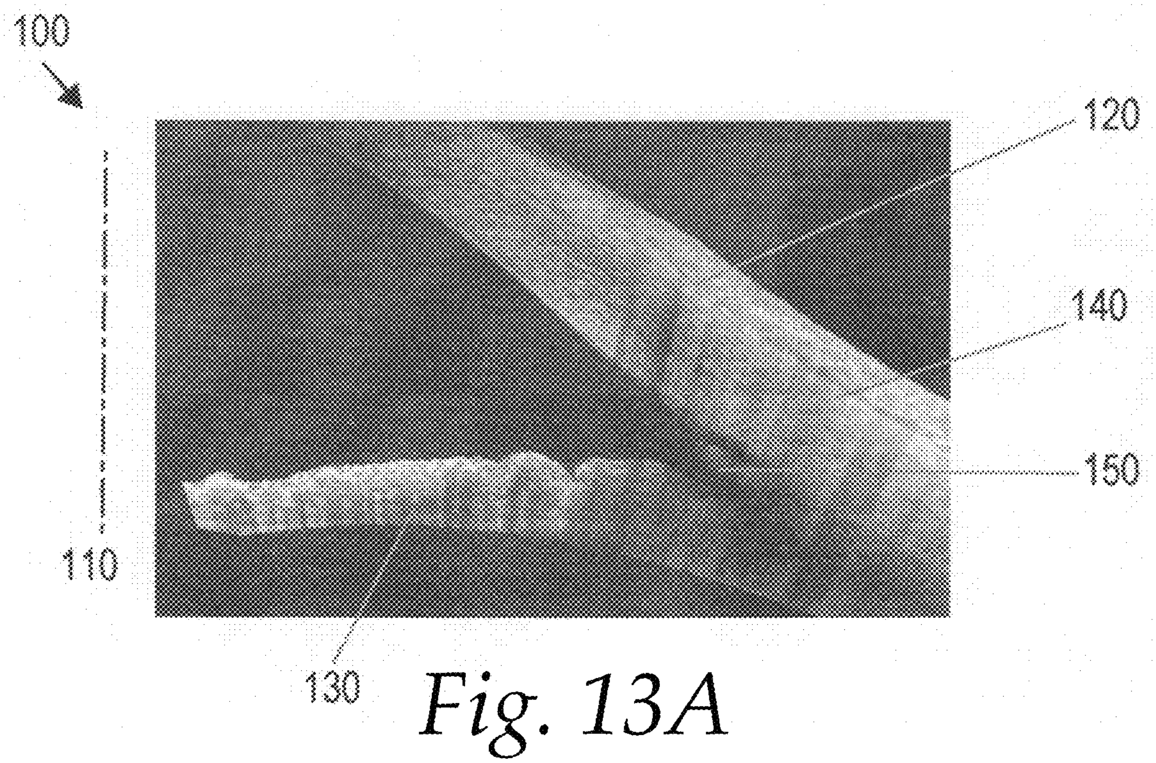
FIG. 13A is an optical coherence tomography image of an eye subsequent to an operation with an instrument according to the present invention.
Figure 13B:
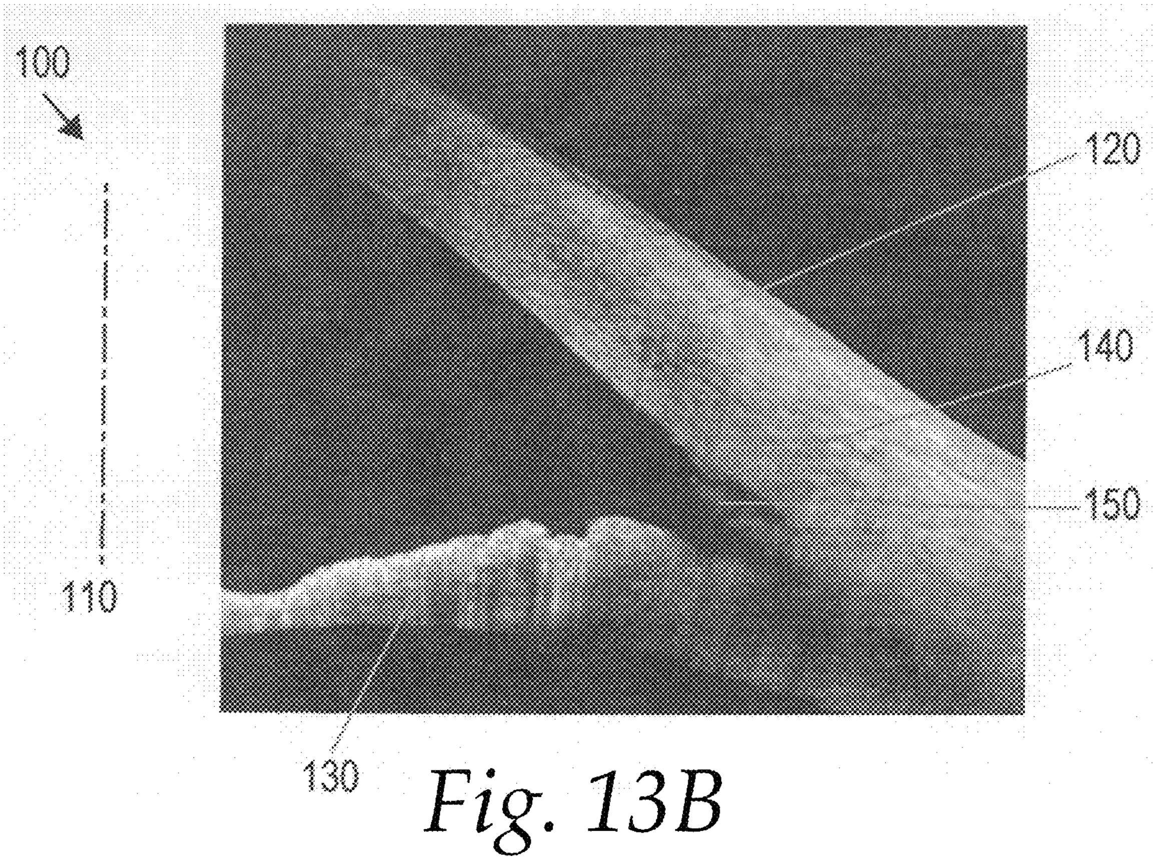
FIG. 13B is an optical coherence tomography image of an eye subsequent to an operation with an instrument according to the present invention.
Figure 13C:
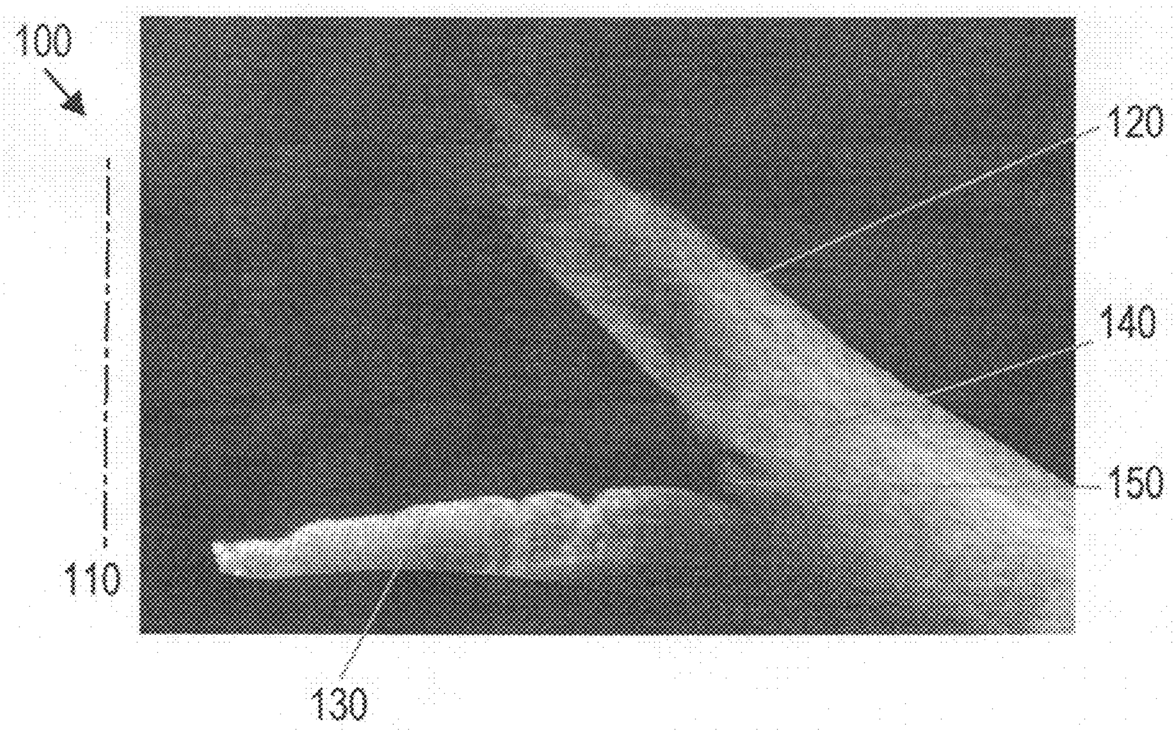
FIG. 13C is an optical coherence tomography image of an eye subsequent to an operation with an instrument according to the present invention.
Figure 13D:
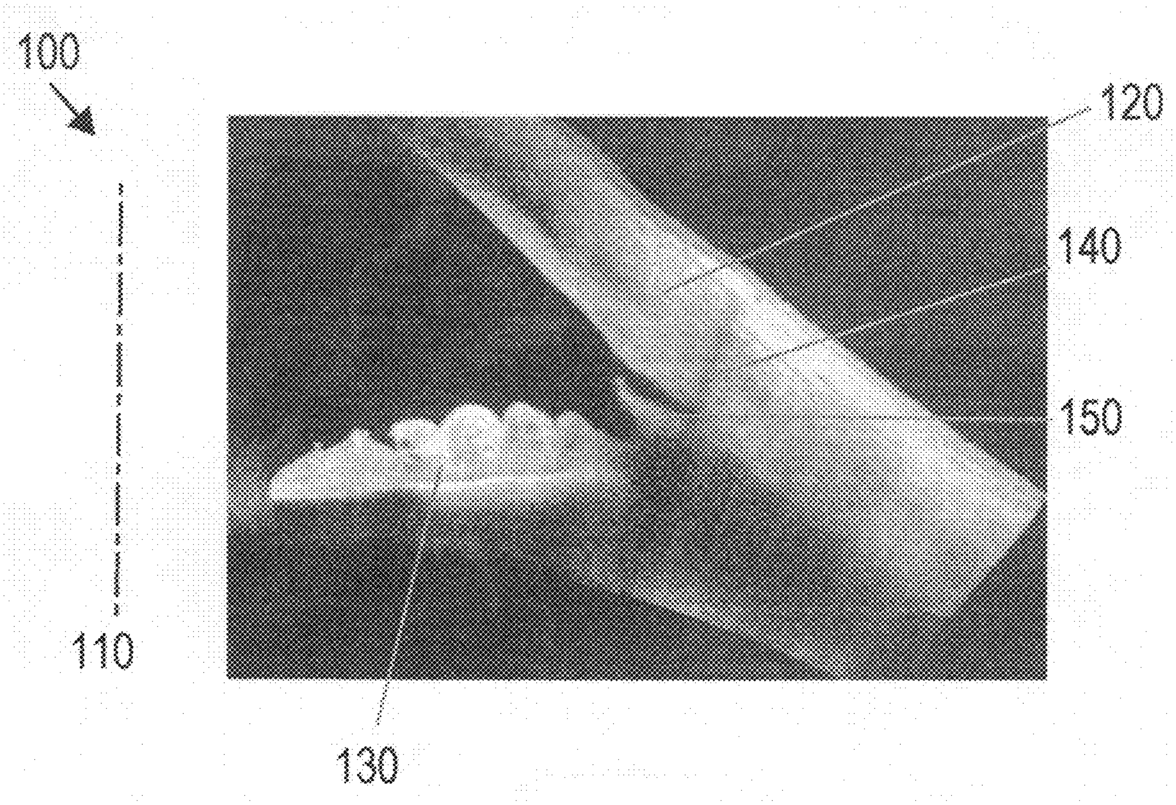
FIG. 13D is another optical coherence tomography image of an eye subsequent to an operation with an instrument according to the present invention.

FIG. 13A shows the eye 100 after 1 month from the date of the surgery with the instrument 40 of the present invention, FIG. 13B shows the same eye 100 after 12 months from the date of the surgery, and FIG. 13C shows the same eye 100 after 17 months from the date of the surgery. FIG. 13D shows a classic appearance of the trabecular vent in the eye 100 following an iVent surgery with the present invention. The acute angle of the trabecular corneal angle is classic for a post operative appearance of the vent created with the inventive technique, whereby the leaflet 150 rotates in a posterior direction along the optical axis upon severing the anterior attachment portion of the trabecular meshwork. The appearance of this trabecular vent angle is distinctly different from the appearance of angles after other forms of goniotomy, GATT, OMNI, etc.

Figure 13E:
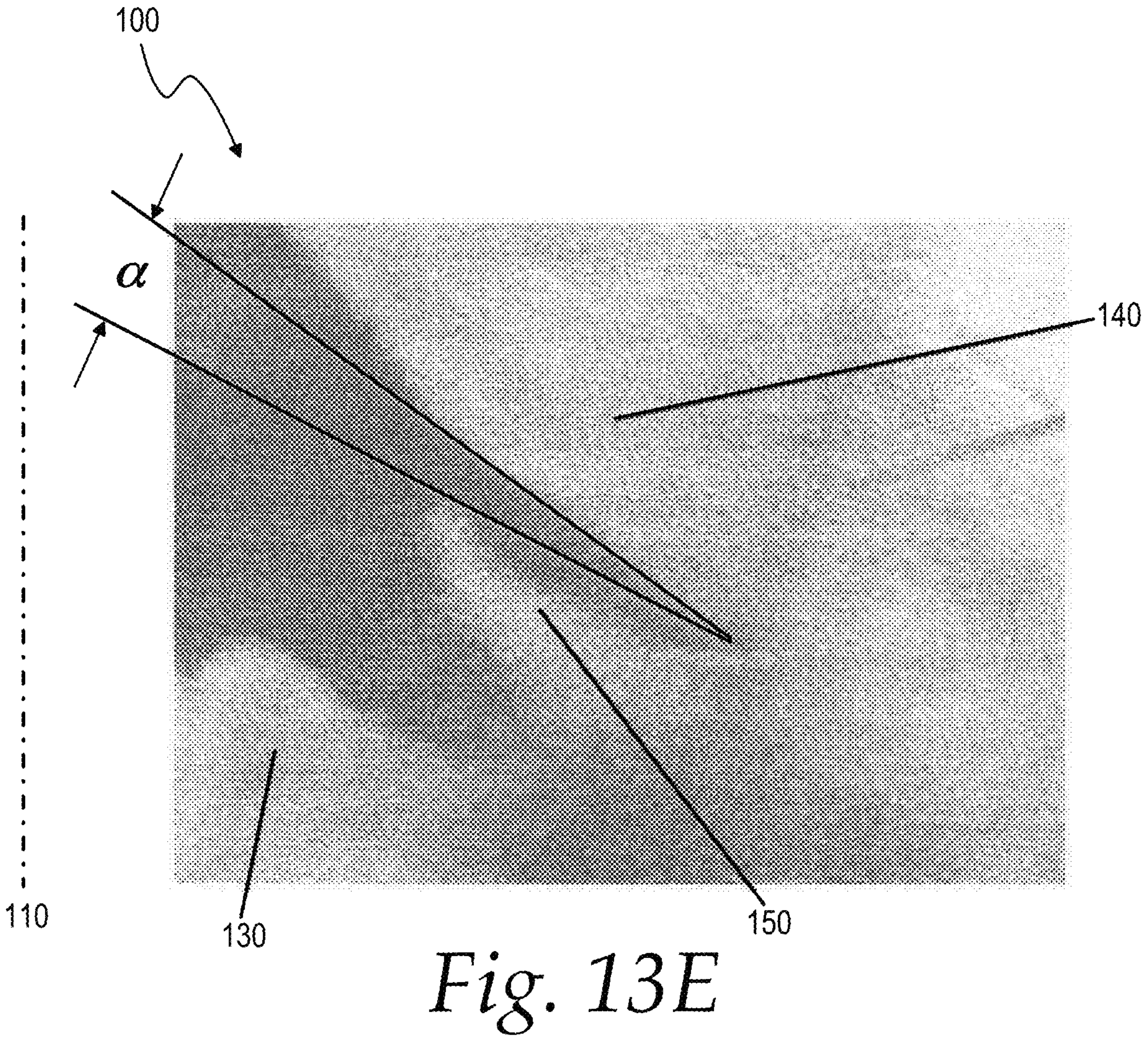
FIG. 13E is a greatly enlarged portion of the image of the eye of FIG. 13D.
Figure 13F:
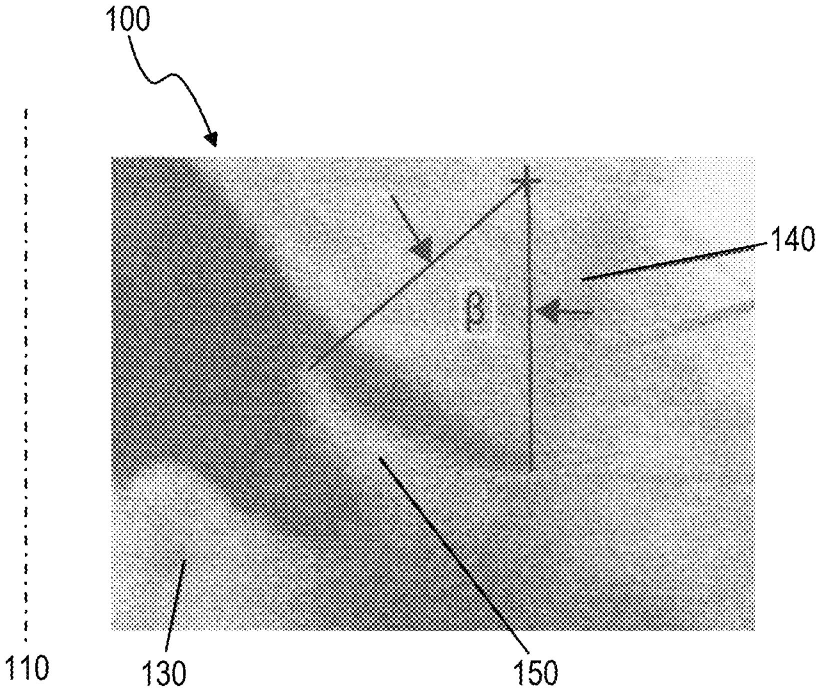
FIG. 13F is a greatly enlarged portion of the image of the eye of FIG. 13D.
Figure 13G:
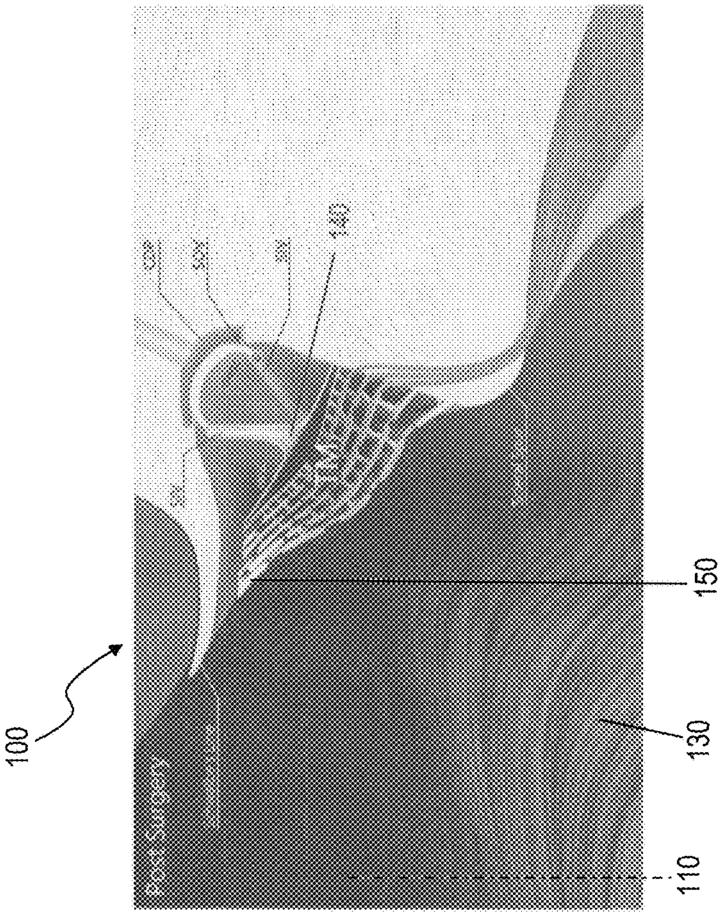
FIG. 13G is a diagrammatic, simplified cross-sectional view of the eye subsequent to an operation with an instrument using the method according to the present invention showing the flow structures and valves behind the trabecular meshwork.

FIG. 13G is a diagrammatic, computer assisted drawing model of the post-operative eye 100 that has been operated upon by the system in the form of the instrument 40. FIG. 13G shows the iris 130, and the opening of Schlemm's Canal 140 and valve structures behind the trabecular meshwork, and the inventive leaflet 150 in the post-operative eye 100. More specifically, it can be seen that the linear cleavage plane of the method of the present invention severs the attachment portion of a portion of the trabecular meshwork and further severs the inner wall of the Schlemm's Canal.

Figure 5:
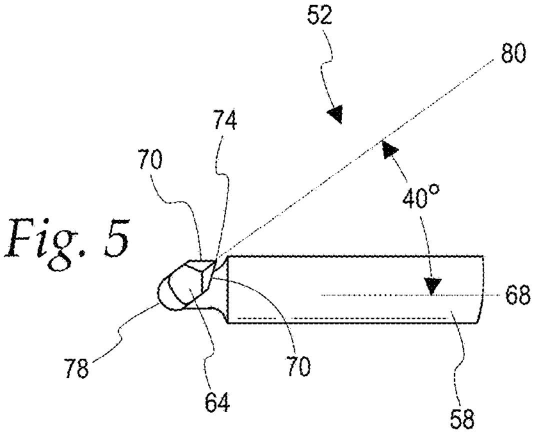
FIG. 5 is a greatly enlarged, fragmentary, left-side elevation view of the distal tip portion of the instrument shown in FIG. 1.
Figure 3:
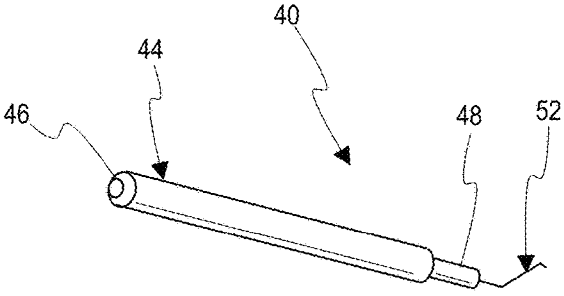
FIG. 3 is an isometric view, taken from above and the right side, of the instrument of FIG. 1.
Figure 6:
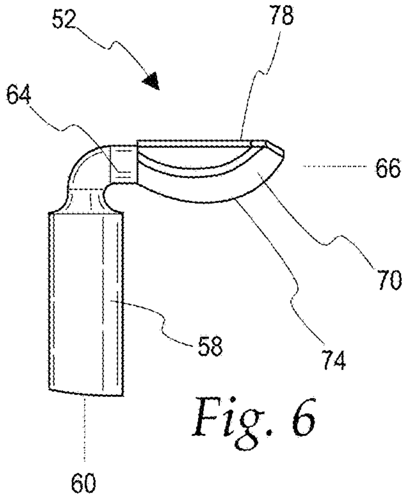
FIG. 6 is a greatly enlarged, fragmentary, top plan view of the distal tip portion of the instrument shown in FIG. 1.
Figure 7:
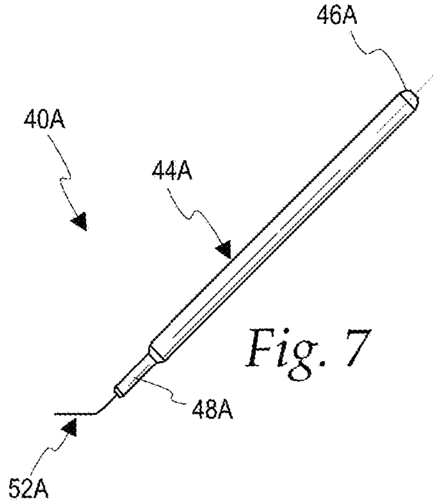
FIG. 7 is a left-side elevation view of a second embodiment of a surgical instrument for performing the method according to the present invention, wherein the instrument has the form of a handheld cutting instrument with a sharpened cutting edge.
Figure 10:
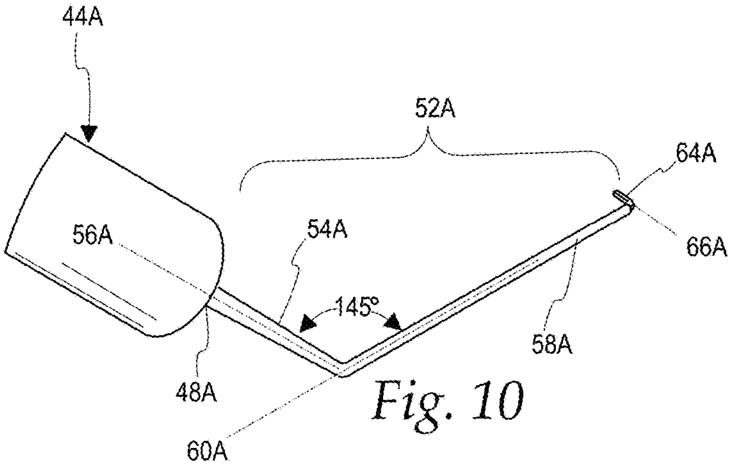
FIG. 10 is an enlarged, isometric view, of the distal portion of the instrument of FIG. 7.
Figure 8:
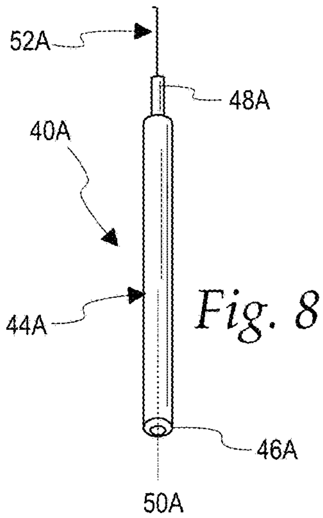
FIG. 8 is a top plan view of the instrument of FIG. 7.
Figure 11:
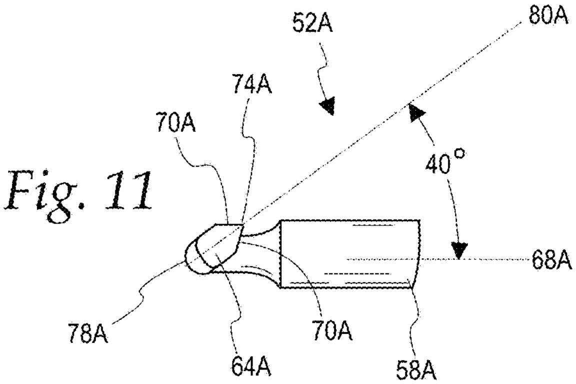
FIG. 11 is a greatly enlarged, fragmentary, left-side elevation view of the distal tip portion of the instrument shown in FIG. 7.
Figure 9:
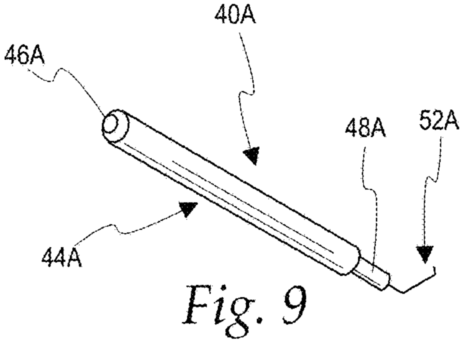
FIG. 9 is an isometric view, taken from above and the right side, of the instrument of FIG. 7.
Figure 12:
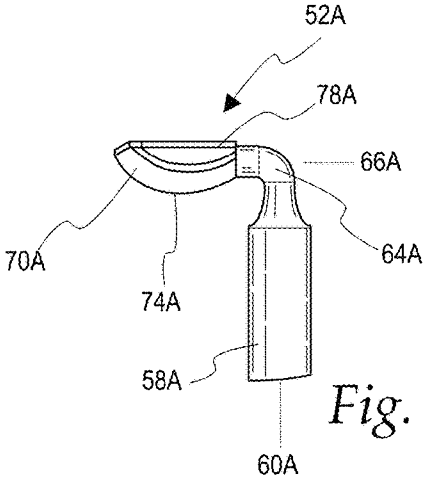
FIG. 12 is a greatly enlarged, fragmentary, top plan view of the distal tip portion of the instrument shown in FIG. 7.
Figure 12A:
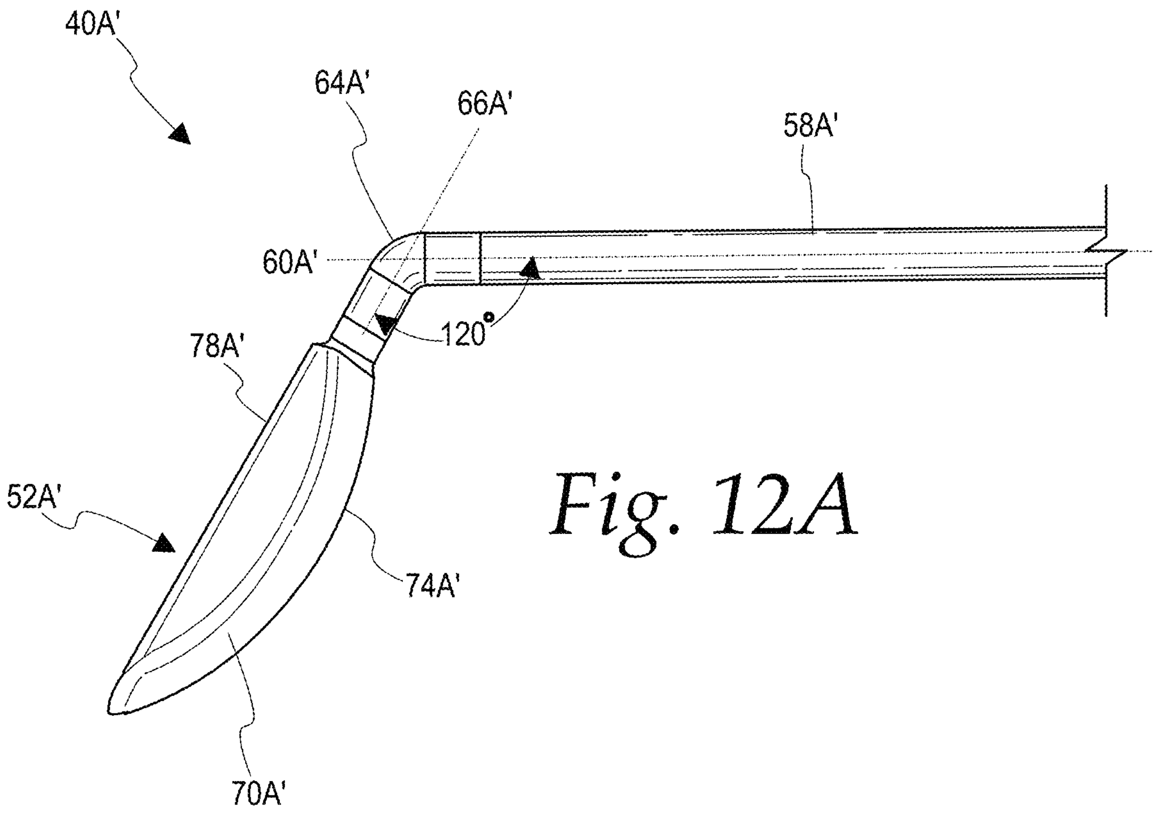
FIG. 12A is a greatly enlarged, fragmentary, top plan view, of a distal portion of a variation of the second embodiment of a surgical instrument for performing the method according to the present invention, wherein the instrument has the form of a handheld cutting instrument with a sharpened cutting edge.
Figure 12B:
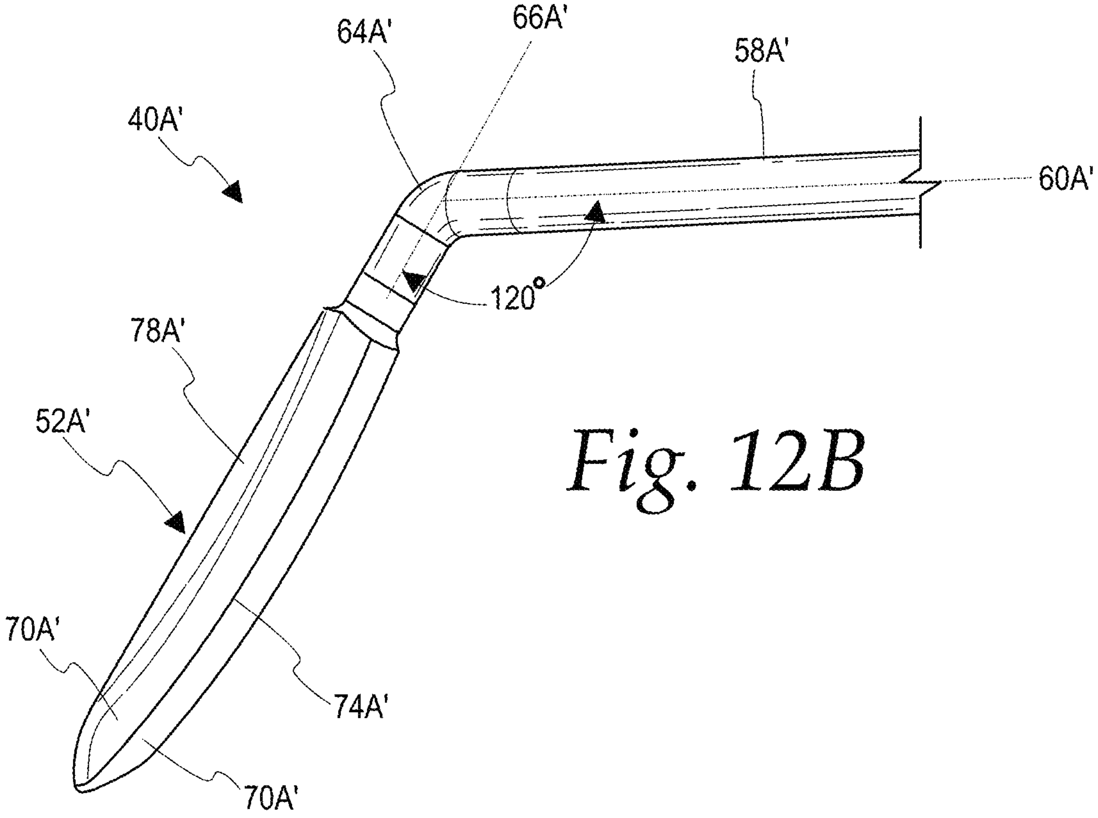
FIG. 12B is a greatly enlarged, isometric view from above, of the distal portion of the instrument shown in FIG. 12A.
Figure 12C:
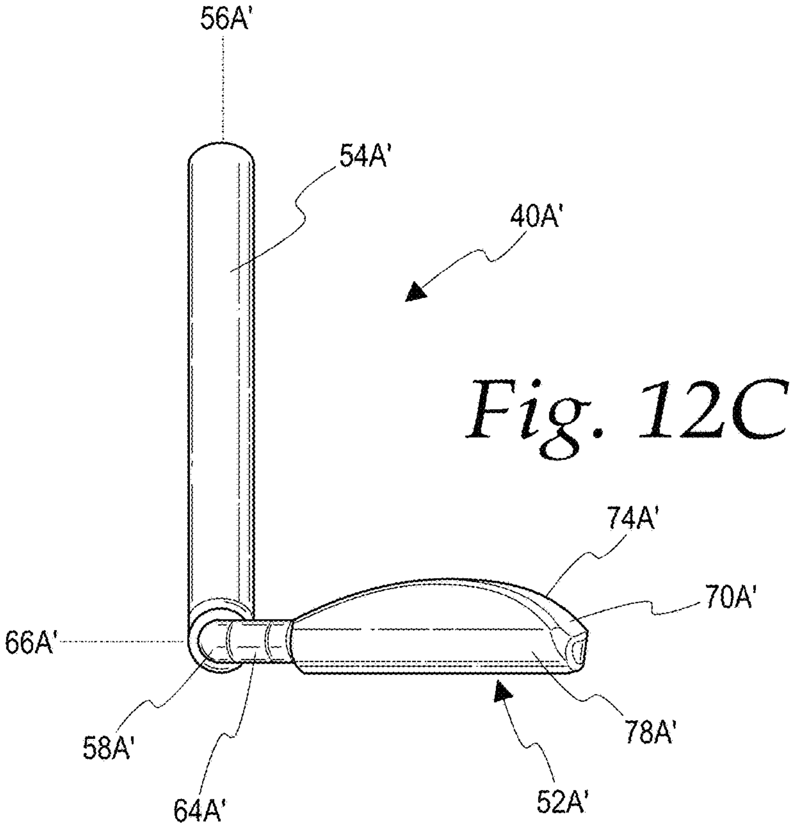
FIG. 12C is a greatly enlarged, fragmentary, rear elevation view of the instrument shown in FIG. 12A.
Figure 12D:
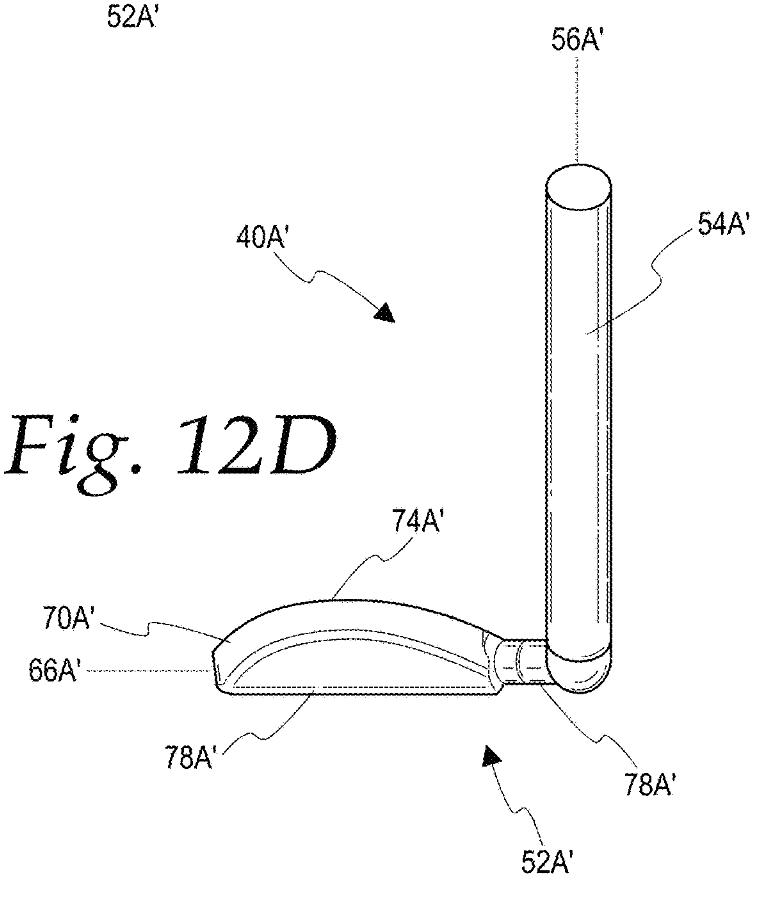
FIG. 12D is a greatly enlarged, fragmentary, front elevation view of the instrument shown in FIG. 12A.
Figure 12E:
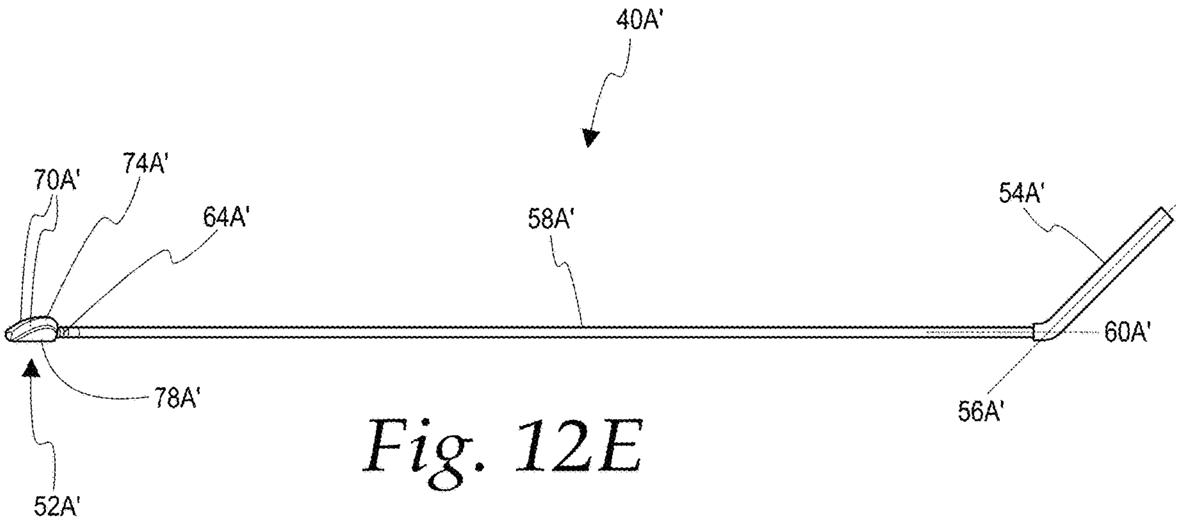
FIG. 12E is a greatly enlarged, fragmentary, left-side elevation view of the instrument shown in FIG. 12A.
Figure 12F:
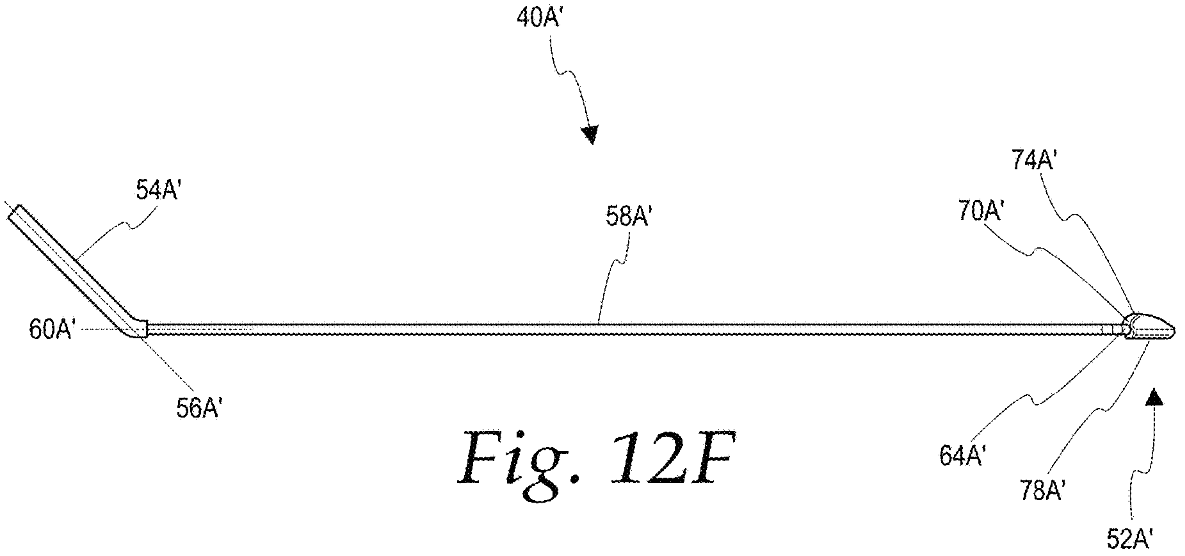
FIG. 12F is a greatly enlarged, fragmentary, right-side elevation view of the instrument shown in FIG. 12A.
Figure 12G:
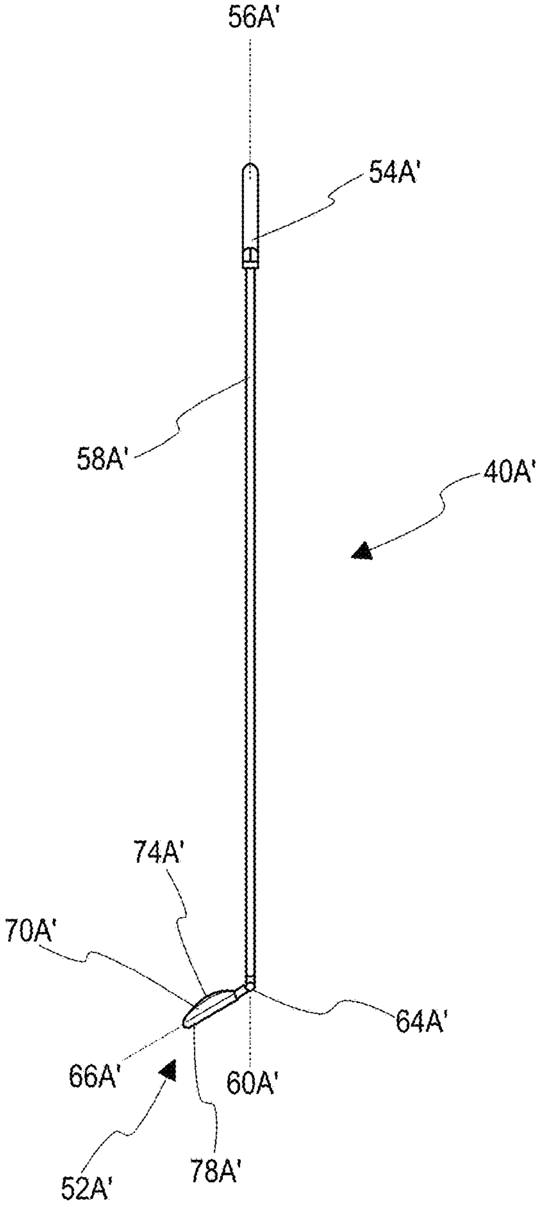
FIG. 12G is a greatly enlarged, fragmentary, bottom plan view of the instrument shown in FIG. 12A.
Figure 12H:
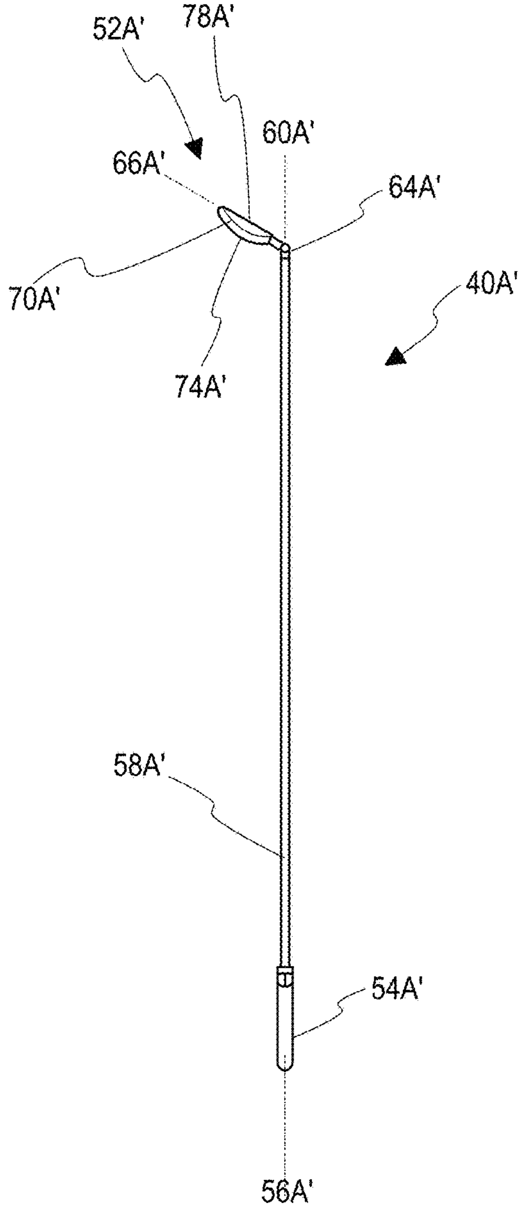
FIG. 12H is a greatly enlarged, fragmentary, top plan view of the instrument shown in FIG. 12A.

With reference now to FIGS. 5 and 6, the preferred cutting means of the instrument 40 has the form of a pair of sloping, arcuate cutting surfaces 70 that join to define an arcuate cutting edge 74. The cutting surfaces 70 are preferably semi-circular and define a bevel terminating rearwardly to face the hand grip 44 of the instrument 40 when gripped by a user. As can be seen in FIG. 5, the instrument 40 defines a plane 68 that contains the axes 60 and 66 of the intermediate tip portion 58 and the terminal portion 64 of the tip 52. The arcuate cutting edge 74 defines a central edge axis 80 that is angled between about 30 and 50 degrees, and more preferably about 40 degrees relative to the plane 68. The distal most end of the terminal portion 64, relative to the hand grip 44, is a blunted surface 78 that is opposite the arcuate cutting edge 74. The blunted surface 78 is the furthest portion of the tip 52 away from the hand grip 44.

With reference to FIG. 5, the terminal portion 64 of the tip 52 preferably has a width of about 0.1 mm.

With reference to FIG. 6, the terminal portion 64 of the tip 52 preferably has an operative blade length of about 0.30 mm, along the terminal portion axis 66 and a blade width of about 0.15 mm in the direction normal to the axis 66.

Other configurations of the cutting edge of the surgical instrument are contemplated.

The inventors of the present invention believe that the embodiments of the instrument discussed herein may advantageously permit the surgeon to improve flow through the outflow tissues by disinserting the trabecular meshwork from Schwalbe's line and simultaneously preserving the valve like function inherent to the outflow system. The instruments herein may lower costs for the glaucoma procedure compared to existing surgical instruments with expensive handpieces, and may improve surgical outcomes by reducing the time of the procedure compared to surgeries performed with prior art devices. The instruments disclosed herein may be easier to use by a surgeon, cost less than leading prior art devices on the market, and/or reduce or eliminate post-operative visits to the surgeon by the patient.

The present invention facilitates the creation of a unique incision into the trabecular tissue compared to all other currently know methods for opening the trabecular meshwork, including but not limited to Kahook Dual Blade, OMNI 360 Surgical System, iStent inject, Hydrus, GATT, Hemi-GATT and Tanito Goniotomy. An advantage of the present invention include the precise and selective opening of the anterior most aspect of the trabecular meshwork, essentially just posterior to Schwalbe's line. This selective incision of the trabecular meshwork allows for the cleavage of trabecular meshwork tissue with minimal disruption of the existing intracanalicular valvular system. The cleaved trabecular meshwork is detached from Schwalbe's line, but remains attached to the scleral spur. Depending on the elasticity of the leaflet and other factors including gravity and postoperative healing, the leaflet remains open to varying degrees. This selective anterior cleavage of the trabecular meshwork protects disruption of the microscopic support structures in the angle and theoretically preserves the pump/valve function within Schlemm's Canal.

A further advantage of this procedure is to minimize trauma and preserve the valve system unlike the Kahook Dual Blade, iTrack, Omni 360, GATT prior art, Tanito, Espaillat, trabeculotomy or ABiC procedures. With minimal disruption of the microscopic support structures within Schlemm's Canal in the present invention, the potential for reflux of blood due to hypotony is minimized (given that the valve structures remain essentially intact). Additionally, because there is no device or instrument that rubs along or disrupts the back or outer wall of Schlemm's Canal, this device also minimizes the risk of disrupting the endothelium lining of Schlemm's Canal, any associated vascularized tissue and any of the microscopic intracanalicular canal structures such as valves and microtubes. Also, depending on the degree of glaucomatous disease and valvular dysfunction, the specific cleavage plane created in the anterior trabecular meshwork may allow for a stretching of the intracanalicular valve system with improvement in its function. Further, the unique design of the device allows for maintenance of the anterior chamber.

The inventors have termed the unique method of the subject invention interventional Valve Enhancing Trabeculotomy or "iVent" or "iVEnT". The iVent makes a precise cleavage in the anterior aspect of the trabecular meshwork. Care is taken to avoid the intracanalicular structures and valves when creating this cleavage plane. By specifically cleaving the anterior trabecular meshwork and inner wall of Schlemm's Canal a vent is created.

In regard to traction, by just incising the trabecular meshwork, the anterior attachment is released, and the posterior aspect of the trabecular meshwork shifts away from the anterior insertion into the corneal/scleral inner wall. The movement of the anterior trabecular meshwork from its insertion site allows for traction on the intracanalicular structures and enhancement of canalicular valve function. By enhancing the pump/valve mechanism, the IOP is lowered through improvement of the traditional outflow pathway. This mechanism of enhancement is specifically unique to iVent.

The iVent is different from other anterior segment angle surgeries as it spares disruption of the intracanalicular structures. The enhancement of the traditional outflow pathway may be considered similar to the enhancement seen after such procedures like selective laser trabeculoplasty or SLT, which also has the potential to enhance or rejuvenate an eye's outflow pathway. The cellular stimulation created by the iVent will also improve the pump mechanism of the intracanalicular valves. Additionally, because the trabecular meshwork is being cleaved and not incised and cored out (as is other type of angle surgeries) the iVent is less disruptive and results in a lower degree of acute intraocular inflammation. A significant population of unique cells with stem cell properties reside at Schwalbe's line as shown by (1) Raviola, G. Schwalbe's line's cells: a new cell type in the trabecular meshwork of *Macaca* mulatta. Invest Ophthalmol Vis Sci.m1982:22:45-56 and (2) Braunger B M, Ademoglu B, Koschade S E, at al., Identification of adult stem cells in Schwalbe's line region of the primate eye. IOVS 2014; 55:7499-7507, which are both incorporated herein by reference in their entireties. These adult stem cells, known as Schwalbe's line cells, may compensate for the loss of trabecular meshwork cells associated with glaucoma. These cells may be directly stimulated by iVent to provide a population of pluripotent stem cells that are capable of differentiating into outflow cells that enhance the physiology of outflow. Cytokine release and other factors related to favorable wound healing from the iVent procedure likely stimulate these stem cells to provide a population of cells to improve outflow.

Importantly, the iVent does not involve implanting a foreign body and as such, there is no concern of displacement of a stent or object. There is no concern of erosion or malfunction with the present invention as with an implant. Given the lack of an implant and the minimally traumatic nature of this technique, the iVent is minimally traumatic to the corneal endothelial cells.

It is presently believed that iVent has a lower risk of abnormal wound healing as a result of being less destructive to the trabecular meshwork, as compared to the other prior art techniques mentioned above. The iVent further does not remove valve and channels of the trabecular meshwork, nor does it obstruct or close down such channels.

The iVent surgery has been found by the inventors to lower the intraocular pressure to the low teens when the patient is on one, or on no medications (i.e., medicated drops). The outcomes the inventors are seeing with iVent appear to be distinctly different from the outcomes we have seen with KDB, Trabectome, OMNI, hydrus and istent or other angle based surgeries. These prior art mentioned surgeries tend to have a more modest IOP lowering that results in a postoperative IOP in the mid-teen range with the patient on 1-2 medications. The fact that the inventors are seeing significantly lower eye pressures following the iVent surgery speaks to the novel and unique nature of this surgery and how it specifically enhances the patient's natural outflow pathway through improving the function of the intracanalicular pump/valve mechanism.

It will be understood that the instruments disclosed herein may be formed in a variety of sizes for small incision glaucoma surgery or regular glaucoma surgery.

In one presently preferred method of use of the instrument 40 may be configured for use in incising the nasal angle or temporal angle of the right eye and/or the left eye. The instrument 40 may be inserted through an incision in the cornea of the operative eye. An arc of the trabecular meshwork at (or minimally posterior of) to Schwalbe's line is then engaged by the cutting means of the instrument to create the unique cleavage plane. The trabecular meshwork drops in the posterior direction toward the iris. A gonioprism may be used to view the trabecular meshwork as it is engaged by the instrument 40. Irrigation fluid can optionally be applied on-demand by the user of the instrument 40 in a reflux burst or jet pulse.

Cutting of the anterior trabecular meshwork is achieved by incising just below or at Schwalbe's line. Based on the specific clinical case, the surgeon may selectively incise 1-5 clock hours. Additionally, the surgeon may choose to incise one area, leave an island of untreated trabecular meshwork along the circumference or periphery of the eye, and incise a subsequent area, to maximize canal opening but minimize tissue disruption. This technique creates a unique anterior cleavage plane with the advantages of allowing the trabecular shelf or tissue to remain open and minimize disruption of microscopic structures within the canal. In fact, one could make a small corneal incision in the nasal quadrant and treat the temporal angle 180 degrees, thus creating a 360 degree iVent.

The design of the instrument of the present invention precisely allows for alignment to Schwalbe's line without any difficult positional maneuver for making the incision up to the 6 clock hours (when seating temporal to the patient). This is done easily with the left & right symmetrically designed instruments. If the surgeon were to sit on the opposite side, they could potentially have access to the lateral 6 clock hours and in theory treat 360 degrees if desired, although this approach is not the primary intent of this instrument however the inventors have taken this approach in certain situations.

The inventors believe that the concept that the eye outflow system is a passive filter is outdated. Indeed, Dr. Jorge A. Alvarado found that severe alterations occur in the cellular component and in the entire trabecular meshwork during primary open-angle glaucoma and ageing. The same author demonstrates that trabecular meshwork endothelial cells regulate aqueous outflow by actively releasing enzymes and cytokines that, upon binding to Schlemm's Canal endothelial cells, increase transendothelial flow thereby facilitating the egress of aqueous humour. Trabecular meshwork endothelial cells secrete these factors in response to stimuli such as mechanical stretching, laser irradiation, and pro-inflammatory cytokines.

The inventors of the present invention believe that the instruments and methods of the present invention could be very effective with potential longer lasting results.

Current Understanding of the Mechanism of Action

The present understanding of the inventors of the mechanism of action of the present invention follows, with the understanding that the inventors are not bound by the current theories of operation of the instruments and methods of the present invention.

Motion of outflow tissue is an integral part of outflow resistance and intraocular pressure control. Proper configuration is necessary to optimize the tissue motion which is linked to its tensional status and elasticity. Nestled in the scleral sulcus, and supported by the scleral spur, the outflow tissue is well equipped to mechanosense and respond to the physiologic demands of maintaining the intraocular pressure in a physiologic range. Nearby attachments of ciliary muscle tendons to the scleral spur and the elastin network of the trabecular meshwork/juxtacanalicular connective tissue are important mechanical components of its configuration.

Glaucomatous pathophysiology leads to tissue stiffening, an accumulation of extracellular matrix, and other tissue abnormalities that impair motion. This unfavorable morphology may be improved upon through pharmacologic and/or surgical means, the latter exemplified by canal based microinvasive glaucoma surgery. Improvements in the understanding of the outflow tissue and its associated attachments leads to a more favorable surgical methodology, with a unique mechanism of action. Recent insight demonstrates attention to the surgical incision site creates configurational advantages for the surrounding structures of outflow, besides just creating an incision to increase aqueous flow. This may further reduce intraocular pressure by enhancement of outflow created by improving the configuration of its components.

The iVent treatment method of the present invention lowers intraocular pressure by using a unique surgical instrument with a cutting means to create a tiny linear cleavage plane, or vent, juxtaposed to Schwalbe's line. As seen gonioscopically, wound healing is not excessive for the cleavage plane is made in the non-filtering portion of the trabecular meshwork, the least reactive part of the outflow system. This site is least likely to cause intraocular bleeding. Existing trabecular meshwork cells are not removed and potentially the incision site may stimulate nearby cells to improve outflow. The intracanalicular valves of the outflow system are not damaged for they are typically located in the more posterior filtering portion of the canal. Valve function may be enhanced due to dilation of the canal which creates greater excursions of the valves. Concomitant enlargement of the canal prevents fusion of its anterior and posterior walls, preventing its closure. Severing the anterior attachment of the trabecular meshwork to Schwalbe's line, while leaving the ciliary muscle tendons attached to the scleral spur, allows the ciliary body to rotate the trabecular meshwork-scleral spur complex further inward and posterior. This opens the collapsed trabecular meshwork/juxtacanalicular connective tissue and Schlemm's Canal to the flow of aqueous. Simultaneously, releasing the unwanted tightness of the ciliary body muscle bundles may enhance uveoscleral outflow, a unique combination of trabecular and uveoscleral improvement in outflow. The surface of the trabecular meshwork facing the Schlemm's Canal remains intact after the vent incision. This preserves the oscillating pulse wave's ability to impinge on the trabecular meshwork and drive the trabecular meshwork inward and outward considerably more vigorously, improving the pumping action of the tissue. Much of the glaucomatous process is related to the loss of trabecular meshwork elasticity and resultant Schlemm's Canal collapse. The rotation of the outflow tissue relieves this fundamental causal factor in the pressure elevation of glaucoma. iVent addresses many glaucoma issues well characterized by clinical and experimental studies and the configurational changes reestablish improved anatomy with long-term homeostasis.

It is believed that incising the trabecular meshwork just posterior to the location of Schwalbe's line allows for the creation of a unique trabecular flap, unlike any other created by the prior art instruments. This flap is hinged posteriorly at the scleral spur, however, the angle of opening for the flap below Schwalbe's line is intended to preserve and possibly enhance the intracanalicular structures (i.e., valves, tubules, etc.). These structures are disrupted when a suture, filament or catheter of the prior art techniques are threaded through Schlemm's Canal or when a trabecular shelf is parallel to the iris. However, when a specifically designed spatula that is angled, beveled, and curved is used to create a selective and precise anterior incision in the trabecular meshwork, these intracanalicular structures are preserved and protected. In fact, there is a very high chance that the trabecular meshwork flap being released at its most anterior insertion will provide some tension or stretch on the intra-canalicular valves, a valvulotasis termed by the inventors, and potentially enhance their function.

Relationship Between Elastin of the Trabecular Outflow Pathway, Juxtacanalicular Connective Tissue, Valves, Scleral Spur, and Tone of Ciliary Body Muscle Tendon Network Elastin is a protein located in the connective tissue of the aqueous outflow system. It provides the foundation for an elastic fibrillar network, that in conjunction with ciliary body tendons and other structures, anchors and integrates the trabecular outflow pathway tissue. A complex ciliary muscle tendon network connects to the elastin network at several locations. This overall configuration is especially suited to support a pulsatile pump component of pressure dependent outflow driven by the ocular pulse and especially its impact on the intracanalicular valve system.

Nearby ciliary muscle tendons play important roles in the regulation of aqueous outflow by their elastin connection to the trabecular, juxtacanalicular, canalicular, intracanalicular and circular deep plexus tissues. Ciliary muscle tone is regulated by many factors including the proprioceptive intraocular pressure feedback loops of the autonomic nervous system, mediated primarily by parasympathetic and lesser sympathetic neurotransmission. These neuro transmission points are not violated by the iVent incision site, thus preserving the proprioception of outflow.

Ciliary muscle tendons connected to the elastin network regulate outflow configuration, much like smooth muscle cells control flow through a vessel. Important components of this include trabecular and Schlemm's Canal tissue expansion, distension and intracanalicular valve motion in response to intraocular pressure fluctuations.

The relationship of the anchoring scleral spur to Schlemm's Canal and outflow structures ensures optimal geometry of outflow. Ciliary muscle tendons attach to and modulate scleral spur geometry by altering vector forces that pull it posteriorly and inward to maintain space in Schlemm's Canal. The scleral spur contains specialized myofibroblast type "scleral spur cells" that are directly attached through their scleral spur elastic network to the elastic network of the trabecular outflow system. This may independently assist optimal configuration of the trabecular lamellae and Schlemm's Canal for aqueous outflow. Part of the ciliary muscle tendon network passes near the scleral spur and traverses the trabecular tissue attaching in the vicinity of Schwalbe's line. The coordinated motion of all these outflow configurations, in conjunction with the mechanobiology of the surrounding extracellular matrix, creates a biomechanical sensing unit that utilizes feedback loops to modulate aqueous outflow.

Disease may alter the tension and integrity of the elastin network (tensegrity) and change its distensibility and expansion, interfering with aqueous outflow. As outflow tissue loses its elasticity and becomes more brittle, the outflow tissue becomes more dysfunctional. This significantly impairs outflow motion which interferes with the flow of aqueous through the trabecular outflow system. Over time, this pathophysiology may significantly elevate intraocular pressure, resulting in glaucomatous damage.

The precise iVent incision site cleaves the anterior trabecular meshwork/inner wall of Schlemm's Canal and its attendant tendons from their attachment to Schwalbe's line. The vent by itself immediately reduces outflow resistance. Long-term, excessive pathologic tissue tension is alleviated by the incision site, which improves the elasticity (stress/strain curve) of the elastin tissue network. This allows the complex integrated network of both the ciliary tendons and the elastin outflow network to further reduce outflow resistance.

Additionally, adverse scleral spur vector forces generated by glaucoma are diminished by freeing both the ciliary elastic tendons and elastic fibrils from their tether point at Schwalbe's line. This frees the spur to rotate posteriorly and inward, opening the trabecular meshwork and canal. The special myofibroblast contractile scleral spur cells oriented in an equatorial configuration act in concert and further pull the spur posteriorly and inward. This improvement in the orientation of the scleral spur takes advantage of pulsatile outflow which increases the stroke volume of aqueous throughout the outflow system. This improves the long-term control of intraocular pressure by taking advantage of the pulse generated by the heart.

The most important aqueous outflow structures span the scleral spur to Schwalbe's line, housed in the scleral sulcus, a unique scleral indentation located at the inner limbus. Aqueous outflow resistance is highest in these structures and in glaucoma eyes, the resistance is pathologically increased. The limbus of the eye is vital to outflow and fortunately, this area is accessible to surgical intervention. The trabecular meshwork lamellae stretch from the scleral spur to Schwalbe's line. The trabecular meshwork tissue is physiologically finely tuned to a unique tensile strength to facilitate tissue motion and aqueous outflow. The scleral spur is the pulley that normally keeps the trabecular meshwork lamellae and Schlemm's canal open, preventing the collapse of both structures. Unfortunately, the trabecular meshwork, Schlemm's canal, and the surrounding tissue tend to become brittle and collapse in glaucomatous eyes, significantly decreasing outflow. Studies show Young's modulus of these tissues increase with glaucoma, thus, the tissue becomes more brittle, and the outflow tissue loses its elasticity. Motion dependent outflow likely suffers. In glaucoma, the proper movement of the scleral spur and all of its connected outflow tissue, becomes dysfunctional. The inventors theorize that the scleral spur is abnormally pulled outward (a forward anterior rotation) in glaucomatous eyes, towards Schlemm's canal, reducing its ability to keep the trabecular lamellae and Schlemm's canal open. This is difficult to visualize preoperatively, even with OCT. However, with existing HD OCT imaging software of the angle, the inventors have developed a method to measure the position of the scleral spur relative to the outflow structures, termed SLAM, or Spur Limbal Angle Measurement. A smaller SLAM would tend to mechanically collapse the trabecular meshwork lamellae on itself, decreasing the flow of aqueous to a collapsing Schlemm's canal. This likely occurs in glaucomatous eyes because the trabecular meshwork lamellae, which normally stretch across to Schwalbe's line, mechanically overpull the scleral spur outward, towards Schlemm's canal, causing the outflow tissue to collapse upon itself, which pathologically increases outflow resistance. With iVent, the spur angle, or SLAM increases. This increase in angle opens the trabecular meshwork lamellae and Schlemm's canal, decreasing outflow resistance and lowering IOP. The inventors theorize the scleral spur is no longer tethered abnormally to Schwalbe's line and thus is no longer pulled outward toward Schlemm's canal and no longer collapsed. By comparing the pre- and post-iVent nasal to temporal SLAM, it is apparent that iVent increases the nasal spur angle relative to Schlemm's canal/scleral sulcus, opening a collapsed outflow system. The sub-Schwalbe's line incision site also preserves intracanalicular valves. The combination of preserving the valves along with the posterior movement of the scleral spur opens the trabecular meshwork lamellae and Schlemm's canal, a unique mechanism of iVent.

SLAM Methodology

The inventors have developed a method to measure the relative position of the scleral spur to the outflow structures, termed SLAM, or Spur Limbal Angle Measurement, within the confines of the Zeiss 6000 HD angle OCT software.

Vital outflow structures are housed in the scleral sulcus. The scleral spur, seen gonioscopically, constitutes the posterior border of the scleral sulcus. The spur modulate aqueous outflow, especially through its mechanical effect on the outflow structures. However, movement of the spur is not observable during gonioscopy.

The pharmacologically induced posterior movement of the spur is well known to increase trabecular outflow by opening up the collapsed trabecular lamellae and opening Schlemm's canal. The inventors developed the SLAM to compare the unoperated temporal angle to the operated nasal angle, in order to determine if there is a difference in the position of the scleral spur, herewith induced by iVEnT.

Figure 15:
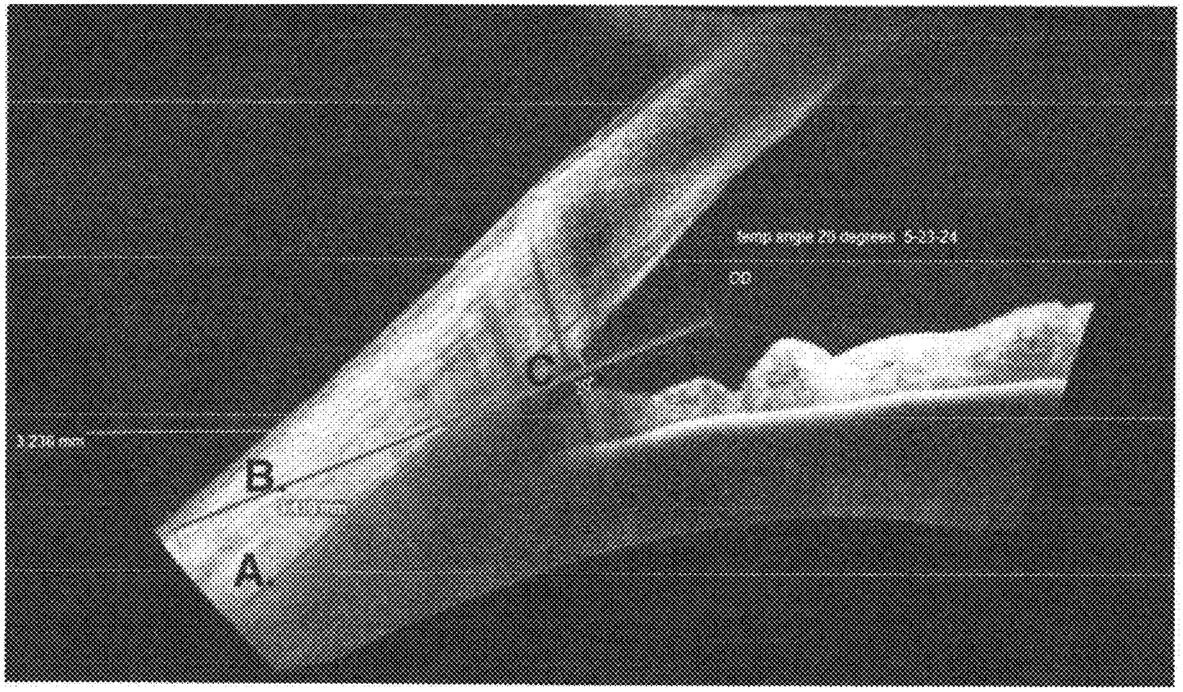
FIG. 15 is another optical coherence tomography high definition image of an eye prior to an operation with an instrument according to the present invention.

Referring now to FIG. 15, the SLAM methodology includes the step of obtaining a high-definition angle OCT image of the nasal and then temporal angle at the horizontal meridian, typically 3 and 9 o'clock at same setting. A 1000 micron calibration ruler is then placed on the image. Using the drop-down ruler, a first line "A" is constructed that parallels the inner sclera posterior to the spur. Using the drop-down ruler, a second line "B" is constructed that parallels the scleral spurline, which intersects line "A". The spur-sulcus angle is thus formed. The resultant angle "C" is then measured with the angle tool software in degrees. Repeat this exercise for the opposite angle, thus constituting a nasal and temporal measurement. FIG. 15 shows an exemplary measurement of an unoperated temporal angle with a SLAM measurement of about 20 degrees.

Figure 16:
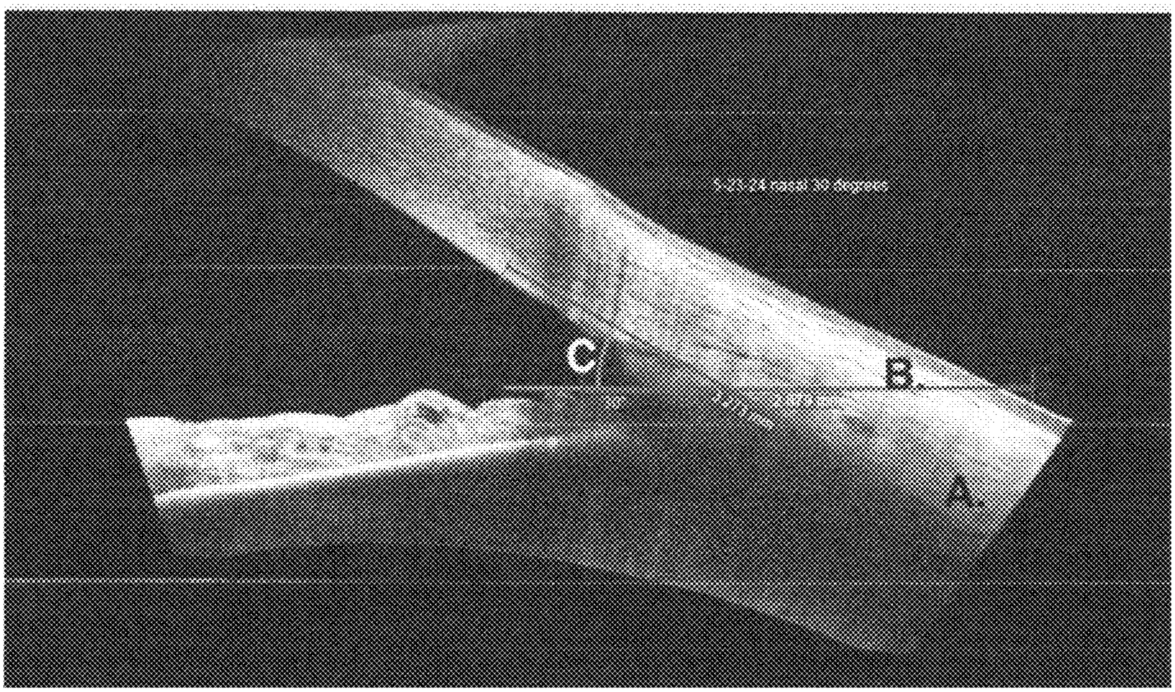
FIG. 16 is another optical coherence tomography high definition image of the eye of FIG. 15 after an operation with an instrument according to the present invention.

Referring now to FIG. 16, it is evident that the nasal operated angle compared to temporal unoperated angle is different. SLAM demonstrates that the nasal spur angle measurement is larger than the unoperated temporal angle, as defined by SLAM. This posterior spur movement, exemplified by a larger SLAM, demonstrates the vector forces from the spur likely pulls open the trabecular meshwork and Schlemm's canal, increasing the flow of aqueous. The sub-Schwalbe's line incision site also preserves intracanalicular valves. The combination of preserving the valves along with the posterior movement of the scleral spur opens the trabecular meshwork lamellae and Schlemm's canal, a unique mechanism of iVEnT. FIG. 16 shows an exemplary measurement of an operated (iVent) nasal angle with a SLAM measurement of about 30 degrees.

The inventors of the present invention have found that the leaflet 150 created by the present invention may be characterized in a number of aspects. A first aspect of the leaflet characterization, with reference to FIG. 13E, is the trabecular meshwork/outer wall of the Schlemm's Canal opening angle $\alpha$. Preferably, the opening angle $\alpha$ is between about 4 degrees and about 45 degrees when viewed in cross-section in a vertical plane that that contains the optical axis 110 of the eye and extends through the incision as shown. More preferably, the opening angle $\alpha$ is about 10 degrees (+/−5 degrees).

A second aspect of the leaflet 150 characterization, with reference to FIG. 13F, is that the leaflet has an arcuate, concave portion or surface facing the outer wall of Schlemm's Canal. Preferably, the arcuate, concave portion may define a central angle $\beta$ between about 30 degrees and about 60 degrees. Furthermore, the arcuate, concave portion of the trabecular leaflet 150 defines a ratio of arc length to radius of between about 0.5 and 0.9.

The accompanying Table 1 defines the outcomes of iVEnT in terms of IOP control, number of preoperative and postoperative medications and various time points following surgery. In addition, the outcomes are stratified depending on preoperative IOP. A total of 89 eyes underwent phaco-iVEnT. Results were first classified according to the standard definition of success typically used by the FDA and most clinical trials for filtering procedures which is: a 20% reduction in IOP on the same or fewer meds. A preoperative IOP of 16.67±3.84 mm Hg on 2.03 medications was reduced to 12.45±2.83 mm Hg on 0.57 medications (a 21.4% reduction in IOP) at the last follow up. Fifty-seven percent of eyes met the overall success criteria, (51/89 eyes) at a median of 13.6 months. 54/89 eyes were on no medications postoperatively. Percent IOP reduction is not always a very clinically relevant outcome method for a canal-based MIGS when preoperative levels average in the mid-teens. Further refinement was necessary to determine clinical efficacy for canal-based ab interno procedures. The sub analysis revealed that patients with a higher preoperative IOP had a greater reduction in postoperative IOP (a 33% reduction in IOP). In this group, the preoperative IOP of 20.3 mm Hg was reduced to 13.5 mm Hg at 13 months. Preoperative medications were reduced from 1.81 to 0.6. The success in this group was defined as a 20% reduction in IOP on same or fewer meds. The success increased to 25/35 or 73%.

For eyes with an even lower IOP, an improved and more specific definition of success included lower postoperative IOP on fewer medications, stratified by preoperative IOP's of less than or equal to 17 mm Hg, 15-17 mm Hg, and IOP less than or equal to 14 mm Hg. The overall success rate range for these stratified eyes was between 71%-77% at approximately 13 months with an IOP reduction post-surgery between 15%-22%. Of note, 60% of eyes were on no medications after 13 months of follow up, and similarly, medications were reduced from a preoperative level of 2.0 to 0.5 at last follow up.

Table 1 reveals an excellent postoperative outcome success range of 57% to 77% (depending on the criteria for success, see Table 1), IOP reduction range of 15% to 33% (as noted in preoperative stratified groups), and fewer postoperative medications in all groups, at a median of 13 months. The authors feel this table provides more transparency and a more clinically meaningful way of interpreting success following IOP lowering surgeries, especially with MIGS.

The tip 52A includes a terminal portion 64A extending from the intermediate portion 58A along a terminal portion axis 66A that is transverse to the intermediate portion axis 56A. Preferably, the terminal portion axis 66A is angled between about 90 degrees and about 140 degrees relative to the intermediate portion axis 60A, and more preferably is angled about 120 degrees. The terminal portion 64A includes cutting means for creating a remaining trabecular leaflet at, or just posterior of, Schwalbe's line in an eye.

TABLE 1 iVent Outcomes

| Group | No. eyes | Preop IOP mmHg | Postop IOP mmHg | Median % of reduction In IOP | Months Postop (Mean) | Number meds preop | Number meds postop | Success (Criteria specific) | Eyes On No meds | IOP no meds mmHg |
|---|---|---|---|---|---|---|---|---|---|---|
| ALL EYES. Success 20% reduction IOP on same or fewer Meds) | 89 | 16.67<br>(3.84)<br>(9-33) | 12.45<br>(2.83)<br><0.001 | 21.4%<br>(median) | 13.67 | 2.03<br>(0.90)<br>(1-4) | .57<br>(0.88)<br><0.001 | 51/89<br>(57.3%) | 54/89<br>(61%) | 12.48<br>(2.95) |
| 1. IOP ≥ 18 mmHg (success is 20% IOP reduction on same or fewer meds)) | 35 | 20.26<br>(3.14) | 13.54<br>(3.26)<br><0.001 | 33.3% | 12.94 | 1.89<br>(0.93) | 0.61<br>(1.00)<br><0.001 | 26/35<br>(74.3%) | 21/35<br>(60%) | 13.71<br>(3.57) |
| 2a IOP ≤ 17 mmHg (success is fewer meds, lower baseline IOP (same for 2b) | 54 | 14.34<br>(2.03) | 11.74<br>(2.28)<br><0.001 | 18.6% | 14.15 | 2.13<br>(0.87) | 0.54<br>(0.79)<br><0.001 | 40/54<br>(74.1%) | 33/54<br>(61.1%) | 11.70<br>(2.20) |
| 2b. IOP 15-17 mmHg | 28 | 15.93<br>(0.81) | 12.57<br>(2.57)<br><0.001 | 21.8% | 13.60 | 2.04<br>(0.84) | 0.68<br>(0.94)<br><0.001 | 20/28<br>(71.4) | 16/28<br>(57.1) | 12.56<br>(2.53) |
| 3 IOP ≤ 14 mm Hg (9-14) (success is lower IOP than baseline on fewer meds | 26 | 12.63<br>(1.46) | 10.85<br>(1.49)<br><0.001 | 15.4% | 14.73 | 2.23<br>(0.91) | 0.38<br>(0.57)<br><0.001 | 20/26<br>(76.9%) | 17/26<br>(65.4%) | 10.88<br>(1.50) |

Referring now to FIGS. 7-12, another embodiment of the a hand-held, manually operated cutting instrument for performing the method of the present invention is illustrated and designated as 40A. The numbered features of the instrument 40A are designated generally with the suffix letter "A" and are analogous to features of the aforementioned illustrated embodiment of the instrument 40 that share the same number (without the suffix letter "A"). The instrument 40A operates in an identical manner as described in detail above and has the same basic features of a hand grip 44A with a tip 52A including a base portion 54A that extends from the distal end 48A of the hand grip 44A and defines a base portion axis 56A through its geometric center. The base portion axis 56A is substantially parallel to, and coincident with, the central axis 50A of the hand grip 44A. The tip 52A further includes an intermediate portion 58A extending from the base portion 54A along an intermediate portion axis 60A that is transverse or angled relative to the base portion axis 56A. Preferably, the intermediate portion axis 60A is angled between about 130 degrees and 160 degrees relative to the base portion axis 56A, and more preferably angled about 145 degrees. It is further contemplated that this embodiment may be configured as a non-angled, straight instrument.

The embodiment of the instrument 40A differs from the above-discussed first embodiment of the instrument 40 in that the terminal portion 64A is configured as a left-angled instrument relative to the hand grip 44A and the other portions of the tip 52A.

Referring now to FIGS. 12A-12H, a variation of the second illustrated embodiment of the preferred surgical instrument for performing the present method of the invention is illustrated and designated as 40A'. The numbered features of the instrument 40A' are designated generally with the suffix "A" and are analogous to features of the aforementioned illustrated embodiment of the instrument 40A that share the same number (without the suffix letter "A"). The instrument 40A' operates in an identical manner as described in detail above and has the same basic features of a hand grip with a tip including a base portion that extends from the distal end of the hand grip and defines a base portion axis through its geometric center. The base portion axis is substantially parallel to, and coincident with, the central axis of the hand grip. The tip further includes an intermediate portion 58A' extending from the base portion along an intermediate portion axis 60A' that is transverse or angled relative to the base portion axis. Preferably, the intermediate portion axis 60A' is angled between about 130 degrees and about 160 degrees relative to the base portion axis, and more preferably angled about 145 degrees.

The tip 52A' includes a terminal portion 64A' extending from the intermediate portion 58A' along a terminal portion axis 66A' that is transverse to the intermediate portion axis 56A'. The terminal portion 64A' includes cutting means for creating a remaining trabecular leaflet at, or just posterior of, Schwalbe's line in an eye.

The embodiment of the instrument 40A' differs from the above-discussed second embodiment of the instrument 40A in that the terminal portion axis 66A' is angled about 120 degrees to the intermediate portion axis 60A'. The inventors have found that increasing this angle greatly enhances the ability of a variety of users to create the aforementioned leaflet in a left-angled instrument (as illustrated), a right-angled instrument (e.g., as shown with embodiment of the instrument 40 in FIGS. 1-6), or a straight, non-angled instrument where the distal portion of the instrument extends in a plane containing the central axis of the hand grip.

The arcuate cutting edge 74A' is angled about between about 30 degrees and about 50 degrees out of the plane containing the axes 60A' and 66A', and more preferably about 40 degrees out of the plane. It will be understood that the instrument 40A' may be provided as a mirror-opposite, right-angled instrument, whereby the tip 52A' is provided on the opposite side of the axes 56A' and 60A', for incising a different portion or segment of the trabecular meshwork along the circumference of the eye.

Figure 14:
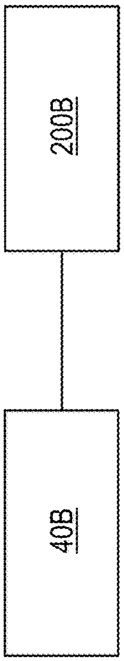
FIG. 14 is a greatly simplified, diagrammatic view of another embodiment of a surgical instrument for performing the method according to the present invention, wherein the instrument may be configured as an invasive or non-invasive laser instrument, vibratory or pulsing cutting instrument, cautery or thermal cutting instrument, trephination surgical instrument, or cryo surgical instrument.

With reference now to FIG. 14 additional embodiments of surgical instruments for performing the method of the present invention are diagrammatically illustrated and designated as 40B with associated equipment (such as power sources, vacuum and irrigation fluid supply, conduits, cords, control hardware and software, etc.) designated as 200B. While the preferred form of the present system is a handheld, manually operated cutting instrument with one or more cutting edges or surfaces to create the trabecular leaflet at, or just posterior of, Schwalbe's line in an eye as described above, the inventors have found that other systems may be used to create a functionally similar leaflet.

In one example, the surgical instrument 40B includes a handheld invasive laser probe that is inserted through the cornea into an area adjacent the trabecular meshwork such as the instruments described in U.S. Pat. Nos. 4,846,172 A and 6,241,721 B1, or other commercially available laser probe surgical systems, which may incise the trabecular meshwork with focused energy in the form of Neodymium: yttrium-aluminum-garnet (Nd:Yag) laser, excimer laser, femtosecond laser, green light laser, diode laser, or other commercially available ophthalmic or medical laser beams. The operation of such laser probe systems and the associated laser generation equipment and associated control software is known in the art and is encompassed generally by element 200B in FIG. 14. The operative or distal end of the laser probe of the surgical instrument 40B must be brought in proximity to the trabecular meshwork and may cut the meshwork to create a trabecular leaflet 150 at, or just posterior of, Schwalbe's line in the eye. The energy of the laser beam and/or the path and extent of the incision may be manually adjusted by the surgeon or may be controlled automatically with associated equipment and control systems. It will be understood that, unlike the mechanical surgical instruments of the present invention, the use of an invasive laser energy probe presents unique difficulties and increased capital equipment costs. For example, non-targeted, surrounding tissues proximate to the trabecular leaflet 150 may potentially be damaged by the laser energy. Furthermore, the laser probe with laser cutting means may not be as maneuverable within the eye as a sharpened microsurgical cutting instrument as described above and may require one or more specialized tip portions to create the requisite angled cleavage of the trabecular leaflet 150.

In another example, the surgical instrument 40B includes a non-invasive laser instrument that is located outside of the cornea and targeted at the trabecular meshwork, with or without an associated lens or mirror located on, or adjacent to, the cornea, such as the instruments described in U.S. Pat. Nos. 6,059,772 A and 11,039,958 B2, and U.S. Patent Application Publication No. US 2020/01468871 A1, which are all incorporated herein in their entireties, or other commercially available laser systems, which may incise the trabecular meshwork with focused energy in the form of Neodymium:yttrium-aluminum-garnet (Nd:Yag) laser, excimer laser, femtosecond laser, green light laser, diode laser, or other commercially available ophthalmic or medical laser beams. The operation of such laser systems and the associated laser generation equipment and associated control software is known in the art and is encompassed generally by element 200B in FIG. 14. The operative or distal end of the laser instrument of the instrument 40B with the laser cutting means must be directed through the cornea, either directly or via a lens or mirror positioned proximate the cornea, and may direct a focused laser into the anterior chamber of the eye to incise the meshwork to create a trabecular leaflet 150 at, or just posterior of, Schwalbe's line in an eye. The energy of the laser beam and/or the path and extent of the incision may be manually adjusted by the surgeon or may be controlled automatically with associated equipment and control systems. It will be understood that, unlike the preferred mechanical surgical instruments discussed above, the use of a non-invasive laser energy instrument presents unique difficulties and increases capital equipment costs. For example, non-targeted, surrounding tissues of the cornea or the tissues proximate to the trabecular leaflet 150 may potentially be damaged by the laser energy. Furthermore, the laser beam may not be as maneuverable within the eye as a sharpened microsurgical cutting instrument as described above.

In still another example, the surgical instrument 40B could have the form of a vibratory cutting instrument having at least one vibratory cutting edge or operative end which is inserted through the cornea and brought proximate to the trabecular meshwork.

The vibratory instrument may be, for example, a longitudinally vibrating phacoemulsification handpiece, a torsionally-vibrating phacoemulsification handpiece, an elliptically vibrating phacoemulsification handpiece, a phacoemulsification handpiece configured for vibratory movement in three dimensions, a vitrectomy handpiece, a piezo electric handpiece, an ultrasound handpiece, a solenoid valve handpiece, pneumatic, or a battery powered handpiece. Other commercially available vibratory handpieces may be used with instrument 40B disclosed herein, which may be suitable to incise the trabecular meshwork as set forth above. The operation of such vibratory cutting instruments and the associated vibration generation equipment and associated control software is known in the art and is encompassed generally by element 200B in FIG. 14. The operative or distal end of the vibratory cutting instrument 40B must be brought in proximity to the meshwork to create a trabecular leaflet 150 at, or just posterior of, Schwalbe's line in an eye. The energy of the vibratory instrument and/or the path and extent of the incision may be manually adjusted by the surgeon or may be controlled automatically with associated equipment and control systems. It will be understood that, unlike the manually-operated mechanical surgical instruments of the present invention discussed above, the use of a vibratory instrument 40B presents unique difficulties and increased capital equipment costs. For example, non-targeted, surrounding tissues of the tissues proximate to the trabecular leaflet 150 may potentially be damaged by the vibratory cutting edge of the instrument. Furthermore, the vibratory cutting instrument may not be as maneuverable within the eye as a manual, sharpened microsurgical cutting instrument as described above.

In yet another example, the instrument 40B includes a cautery, thermal energy, or cryo cutting instrument such as the instruments described in U.S. Pat. Nos. 6,979,328 B2 and 11,464,669 B2, which are incorporated herein in their entireties, such instruments being inserted through the cornea and brought proximate to the trabecular meshwork. Other commercially available surgical instruments may be used with instrument 40B disclosed herein, which may be suitable to incise the trabecular meshwork as set forth above. The operation of such cutting systems and the associated thermal or cryo generation equipment and associated control software is known in the art and is encompassed generally by element 200B in FIG. 14. The operative or distal end cutting means of the cutting instrument of the system 40B must be brought in proximity to the meshwork to create a trabecular leaflet 150 at, or just posterior of, Schwalbe's line in an eye. The energy of the instrument and/or the path and extent of the incision may be manually adjusted by the surgeon or may be controlled automatically with associated equipment and control systems. It will be understood that, unlike the manually-operated mechanical surgical instruments discussed above, the use of a such instruments presents unique difficulties and increased capital equipment costs. For example, non-targeted, surrounding tissues of the tissues proximate to the trabecular leaflet 150 may potentially be damaged by the use of such instruments. Furthermore, such instruments may not be as maneuverable within the eye as a manual, sharpened microsurgical cutting instrument as described above.

Generally, the instruments illustrated and discussed herein may include one or more through passages communicating with an irrigation fluid supply source (either located in a reservoir in the hand grip, or located in an external pressurized container or machine and connected to the hand grip through tubing). The hand grip may include a pressure switch, bellows, or other means to facilitate the selective application of the irrigation fluid from the reservoir or irrigation fluid supply source to a target surgical site or location at the distal, operative end of the instrument proximate the cutting means. Such a hand grip with a reservoir and pressure switch is disclosed in International Application Publication No. WO/2023/018568 of Nallakrishnan, which is incorporated by reference herein in its entirety. Alternatively, an irrigation fluid may be supplied via a sleeve or tube situated around a portion of the instrument. There are many commercially available irrigating handpieces or systems on the market, and it will be understood that the instrument may be adapted to function with such handpieces or systems.

Various modifications and alterations to this invention will become apparent to those skilled in the art without departing from the scope and spirit of this invention. Illustrative embodiments and examples are provided as examples only and are not intended to limit the broadest scope of the present invention.

The invention claimed is:

1. A method of treating glaucoma in an eye, the method comprising the steps of:

obtaining a surgical instrument including a cutting means; and severing (i) an anterior attachment of a portion of the trabecular meshwork of the eye proximate to Schwalbe's line and (ii) the inner wall of Schlemm's Canal with said cutting means of said surgical instrument while leaving the ciliary muscle tendons attached to the scleral spur and preserving the elastic network of the portion of the trabecular meshwork to create a trabecular meshwork/inner wall of Schlemm's Canal leaflet; wherein said step of severing (i) an anterior attachment of a portion of the trabecular meshwork of the eye proximate to Schwalbe's line and (ii) the inner wall of Schlemm's Canal with said cutting means is characterized by a linear cleavage plane severing the attachment portion and the inner wall of Schlemm's Canal which is laterally spaced from, and sparing, the intracanalicular structures and valves of the outflow system of the eye.

2. The method of treating glaucoma in accordance with claim 1, wherein said step of severing (i) an anterior attachment of a portion of the trabecular meshwork of the eye proximate to Schwalbe's line and (ii) the inner wall of Schlemm's Canal with said cutting means is characterized by a linear cleavage plane severing the attachment portion and the inner wall of Schlemm's Canal without removing any of the trabecular meshwork from the eye.

3. The method of treating glaucoma in accordance with claim 1, wherein said trabecular meshwork/inner wall of Schlemm's Canal leaflet rotates in a posterior direction along the optical axis of the eye upon severing the anterior attachment of a portion of the trabecular meshwork.

4. The method of treating glaucoma in accordance with claim 1, wherein said step of severing (i) an anterior attachment of a portion of the trabecular meshwork of the eye proximate to Schwalbe's line and (ii) the inner wall of Schlemm's Canal with said cutting means is characterized by forming an opening angle of between 4 degrees and 45 degrees defined between the trabecular meshwork/inner wall of Schlemm's Canal leaflet and the outer wall of the Schlemm's Canal.

5. The method of treating glaucoma in accordance with claim 1, wherein said surgical instrument including a cutting means is selected from one of: a handheld microsurgical cutting instrument having at least one sharpened edge; a vibratory cutting instrument; or a thermal cutting instrument.

6. The method of treating glaucoma in accordance with claim 1, further comprising the step of applying an irrigating fluid to said trabecular meshwork/inner wall of Schlemm's Canal leaflet.

7. The method of treating glaucoma in accordance with claim 1, wherein said step of severing the anterior attachment of a portion of the trabecular meshwork further comprises severing the inner wall of Schlemm's Canal at an anterior, non-filtering site.

8. The method of treating glaucoma in accordance with claim 1, wherein said step of severing the anterior attachment of a portion of the trabecular meshwork further comprises severing the anterior attachment of a portion of the trabecular meshwork and inner wall of Schlemm's Canal between 90 degrees and 180 degrees around the periphery of the eye.

9. The method of treating glaucoma in accordance with claim 1, wherein said surgical instrument including a cutting means is selected from one of: an invasive or non-invasive laser cutting instrument.

10. A method of treating glaucoma in an eye, the method comprising the steps of:

obtaining a surgical instrument including a cutting means;

severing (i) an anterior attachment of a portion of the trabecular meshwork of the eye proximate to Schwalbe's line and (ii) the inner wall of Schlemm's Canal with said cutting means of said surgical instrument while leaving the ciliary muscle tendons attached to the scleral spur and preserving the elastic network of the portion of the trabecular meshwork to create a trabecular meshwork/inner wall of Schlemm's Canal leaflet; and imaging an angle between said leaflet and said inner wall of Schlemm's Canal.

11. A method of treating glaucoma in an eye, the method comprising the steps of:

obtaining a surgical instrument including a cutting means;

severing (i) an anterior attachment of a portion of the trabecular meshwork of the eye proximate to Schwalbe's line and (ii) the inner wall of Schlemm's Canal with said cutting means of said surgical instrument while leaving the ciliary muscle tendons attached to the scleral spur and preserving the elastic network of the portion of the trabecular meshwork to create a trabecular meshwork/inner wall of Schlemm's Canal leaflet;

measuring a first angle at a temporal location of an unoperated portion of the eye, said first angle defined between an intersection of a first line extending parallel to the inner sclera posterior to the scleral spur and a second line extending parallel to the scleral spur;

measuring a second angle at a nasal location of an operated portion of the eye, said second angle defined between an intersection of a first line extending parallel to the inner sclera posterior to the scleral spur and a second line extending parallel to the scleral spur; and comparing said first and second angles.

* * * * *